United States Patent [19]
Laptewicz et al.

[11] Patent Number: 5,653,684
[45] Date of Patent: Aug. 5, 1997

[54] CATHETER WITH EXPANDABLE WIRE MESH TIP

[75] Inventors: Joseph E. Laptewicz, Eden Prairie; Matthew T. Yurek, Bloomington, both of Minn.; Thomas A. Silvestrini, Santa Clara, Calif.

[73] Assignee: Schneider (USA), Inc., Plymouth, Minn.

[21] Appl. No.: 452,637

[22] Filed: May 25, 1995

Related U.S. Application Data

[62] Division of Ser. No. 210,195, Mar. 19, 1994, which is a division of Ser. No. 904,793, Jun. 26, 1992, abandoned.

[51] Int. Cl.$^6$ ............................................. A61B 17/00
[52] U.S. Cl. ........................ 604/22; 604/107; 606/108
[58] Field of Search .......................... 604/20, 21, 22, 604/104, 105, 106, 107, 280, 281, 282; 606/27–31, 159, 196–200, 194

[56] References Cited

U.S. PATENT DOCUMENTS

| | | | |
|---|---|---|---|
| 5,026,377 | 6/1991 | Burton et al. | 606/108 |
| 5,037,392 | 8/1991 | Hillstead | 604/96 |
| 5,078,720 | 1/1992 | Burton et al. | 606/108 |
| 5,178,618 | 1/1993 | Kandarpa | 606/28 |
| 5,439,446 | 8/1995 | Barry | 604/96 |
| 5,454,365 | 10/1995 | Bonutti | 600/204 |
| 5,456,667 | 10/1995 | Ham et al. | 604/107 |

*Primary Examiner*—John D. Yasko
*Attorney, Agent, or Firm*—Peter C. Richardson; Lawrence C. Akers; Howard R. Jaeger

[57] ABSTRACT

A catheter for use in angioplasty and other medical procedures is disclosed. The catheter features a flexible-wire mesh tip movably attached at a distal end of the catheter, the tip being expandable from a contracted position which it is first in when the catheter is deployed inside the lumen of a vessel, to stretch open the lumen and eliminate a flow obstruction therein, such as is caused by plaque deposits; the tip subsequently being returnable to its contracted position inside the catheter when the catheter is withdrawn from the lumen of the vessel. Radio frequency energy may additionally be used to weld the source of the flow obstruction to the wall of the lumen leaving a conduit of sufficiently expanded diameter to allow resumption of normal flow in the vessel.

21 Claims, 7 Drawing Sheets

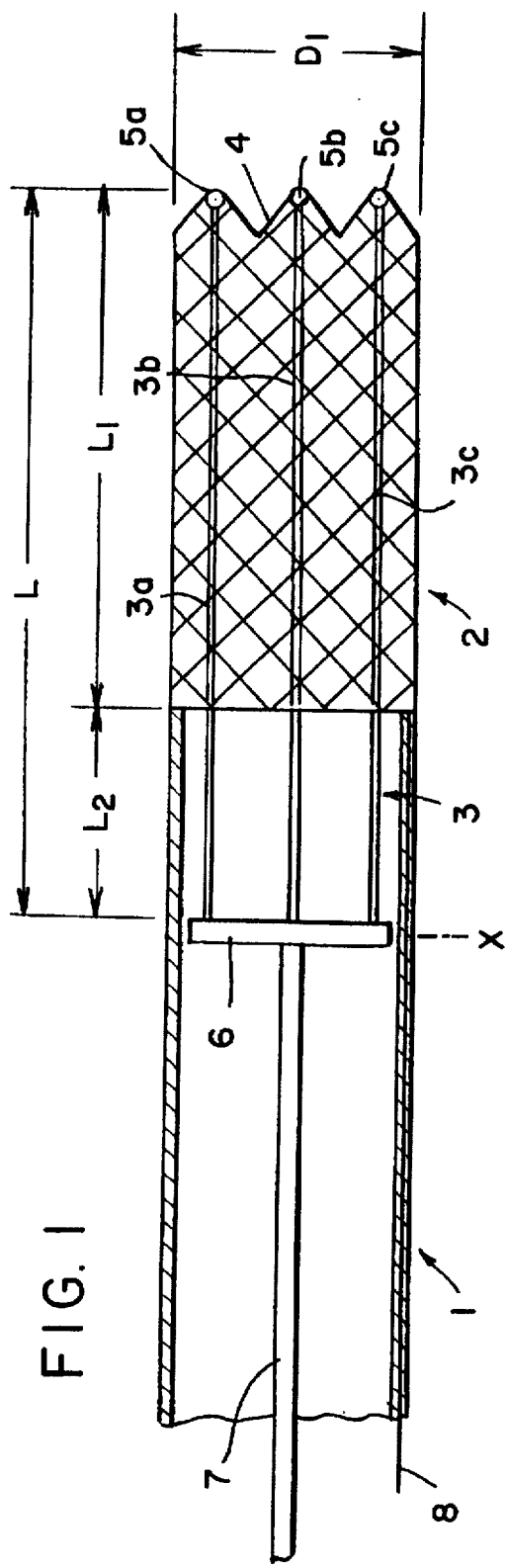
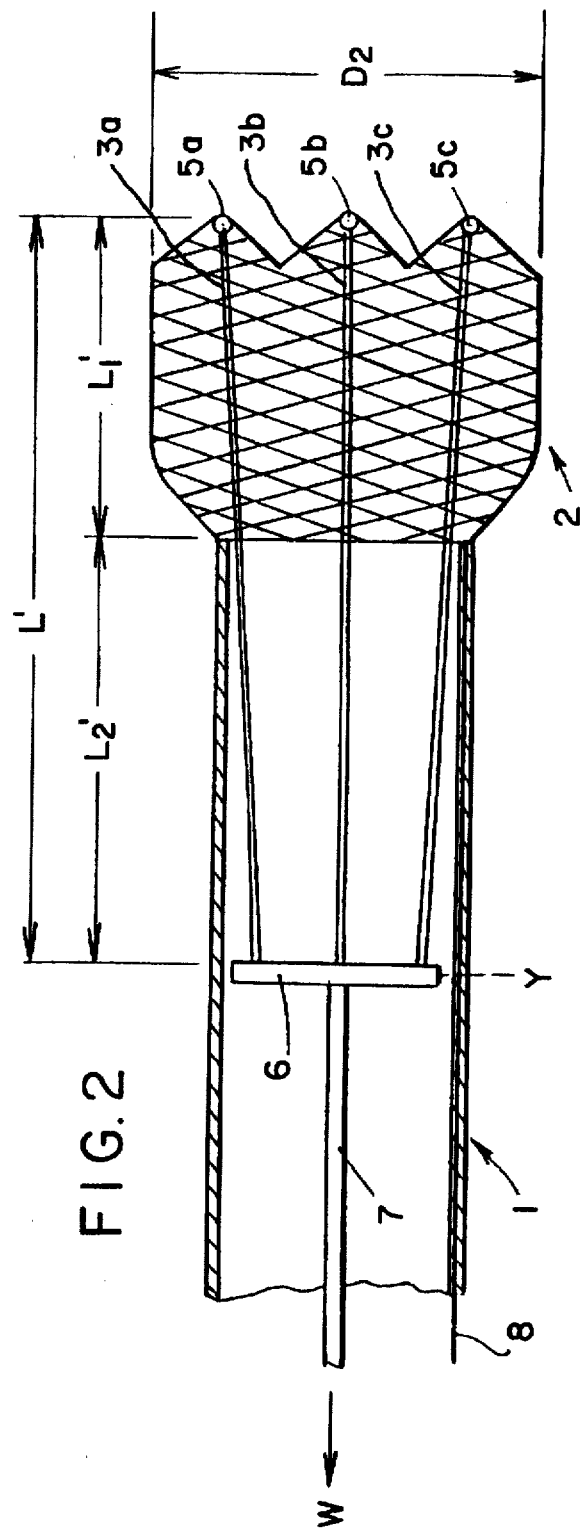

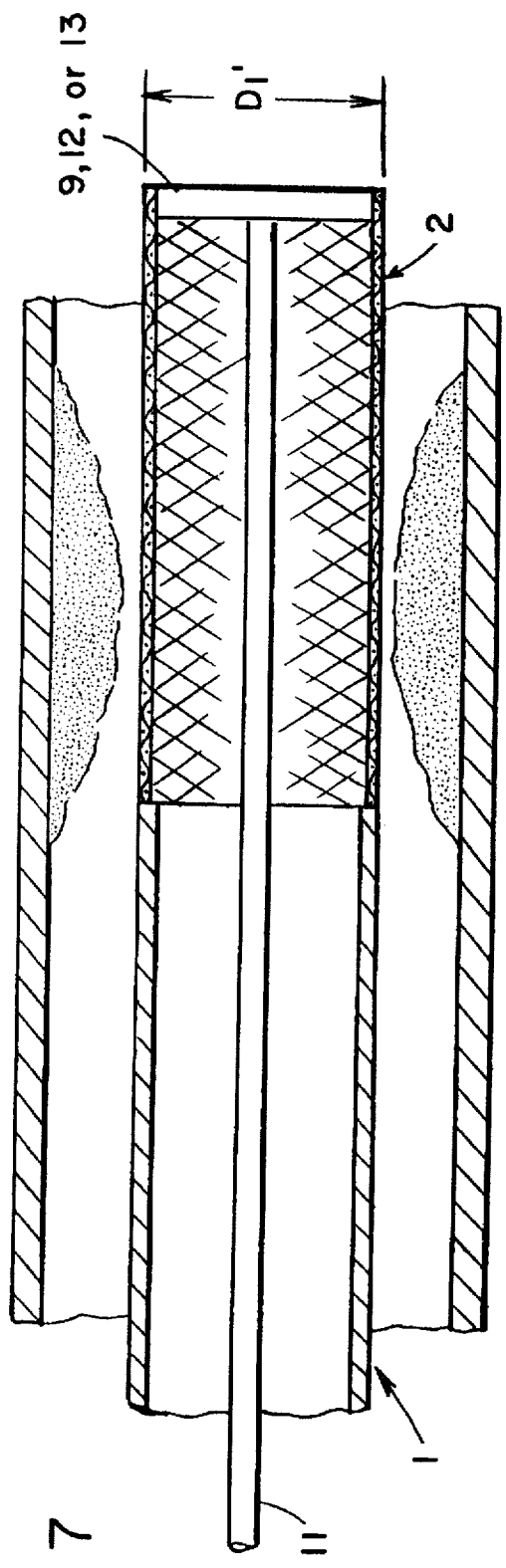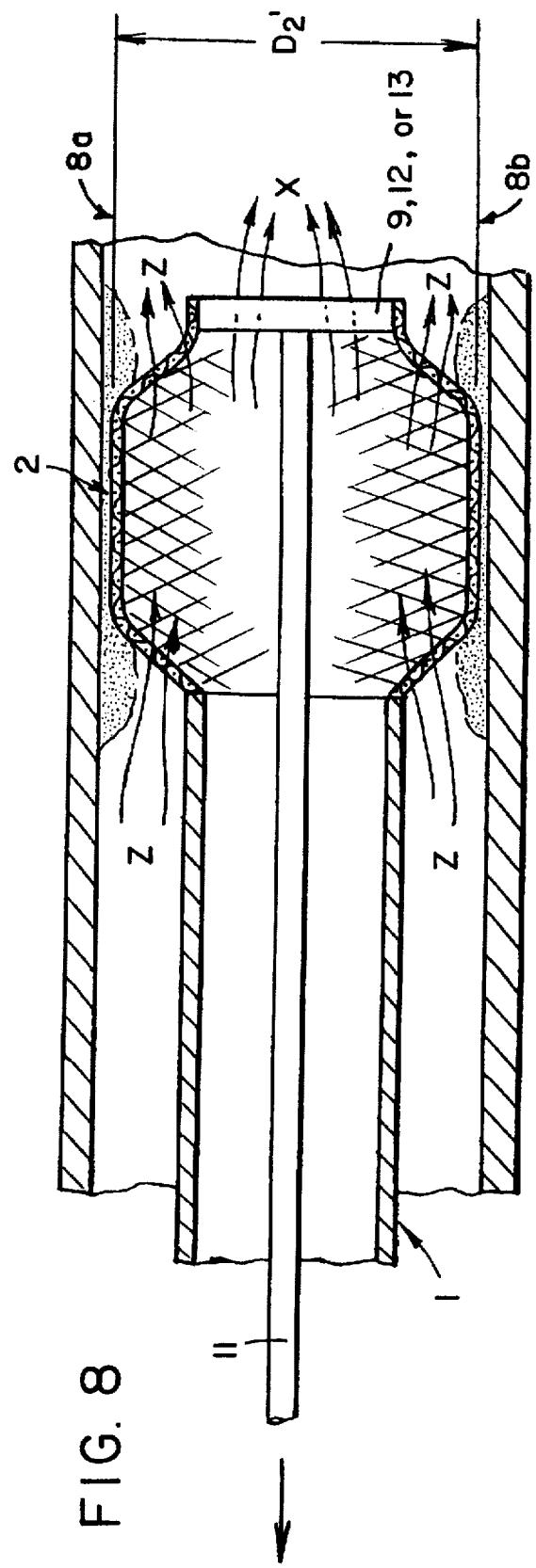

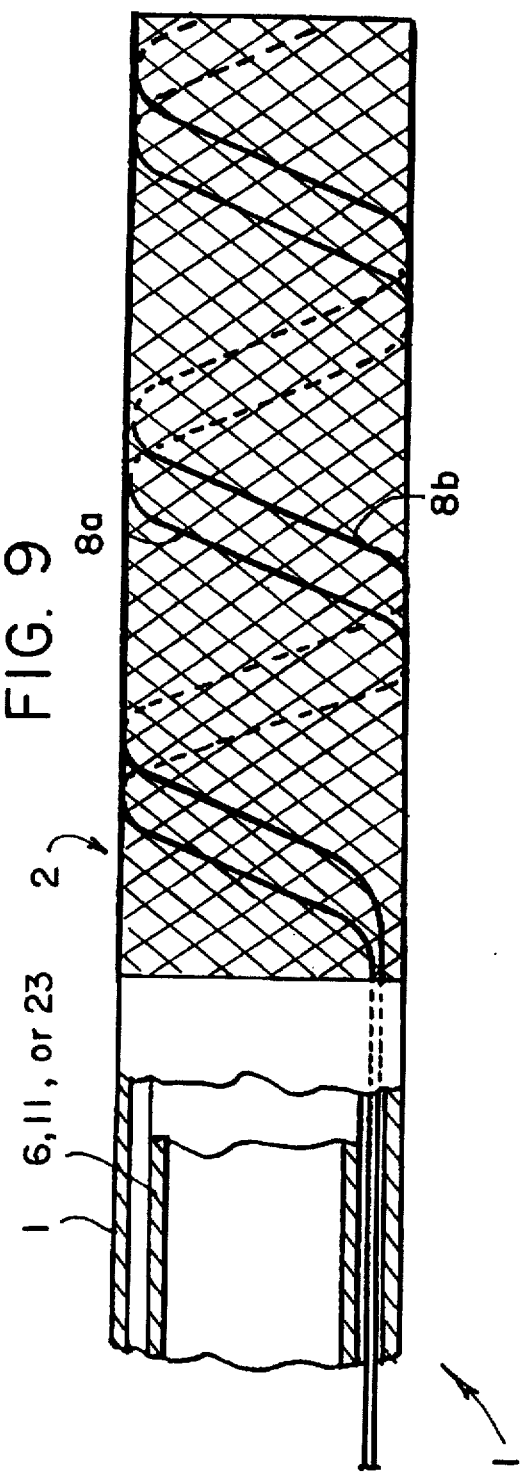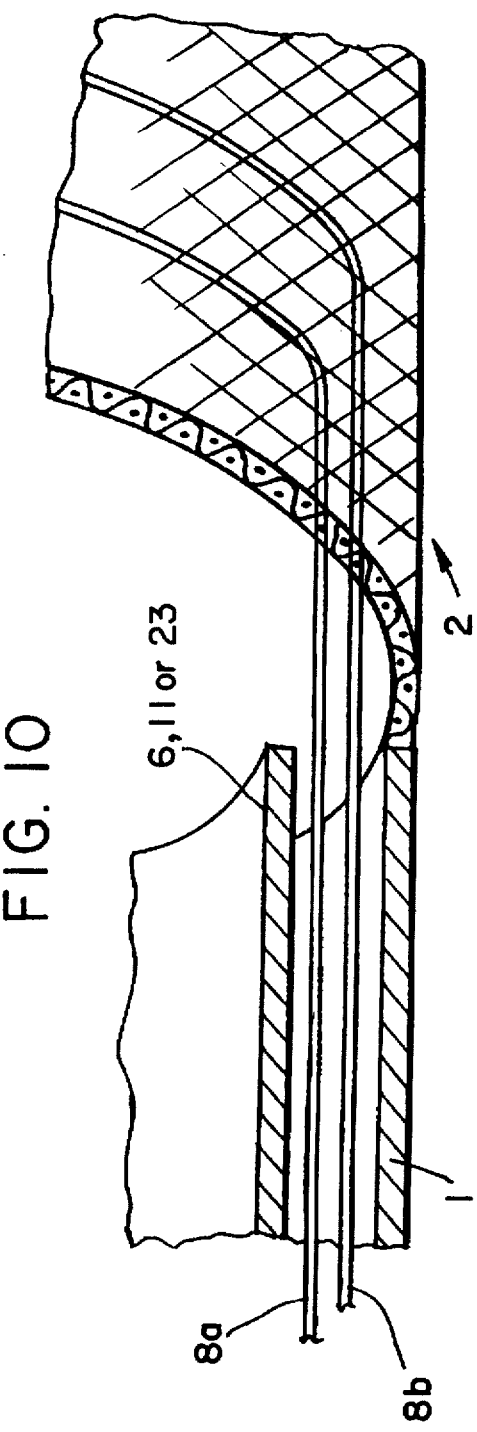

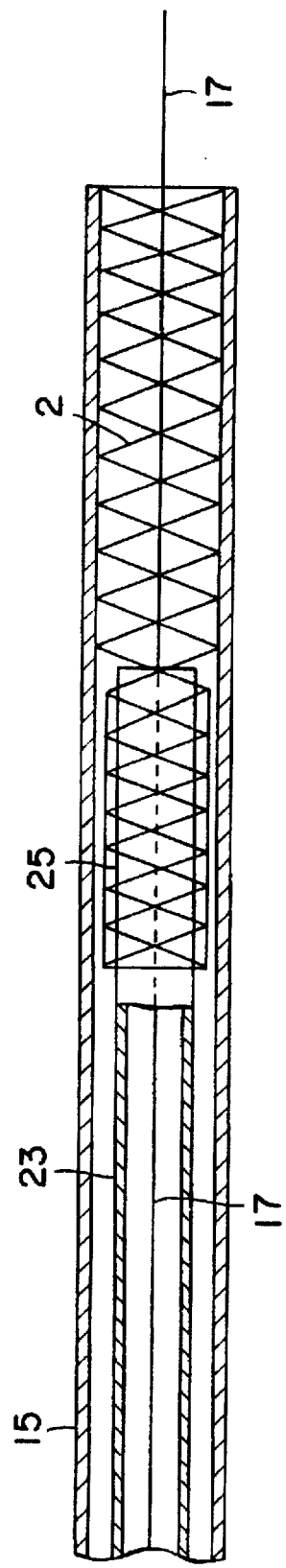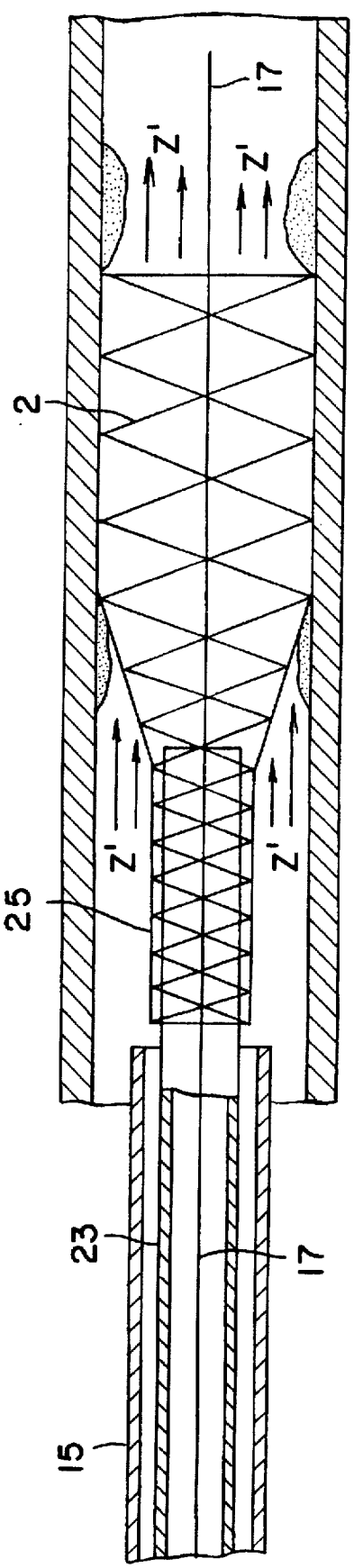

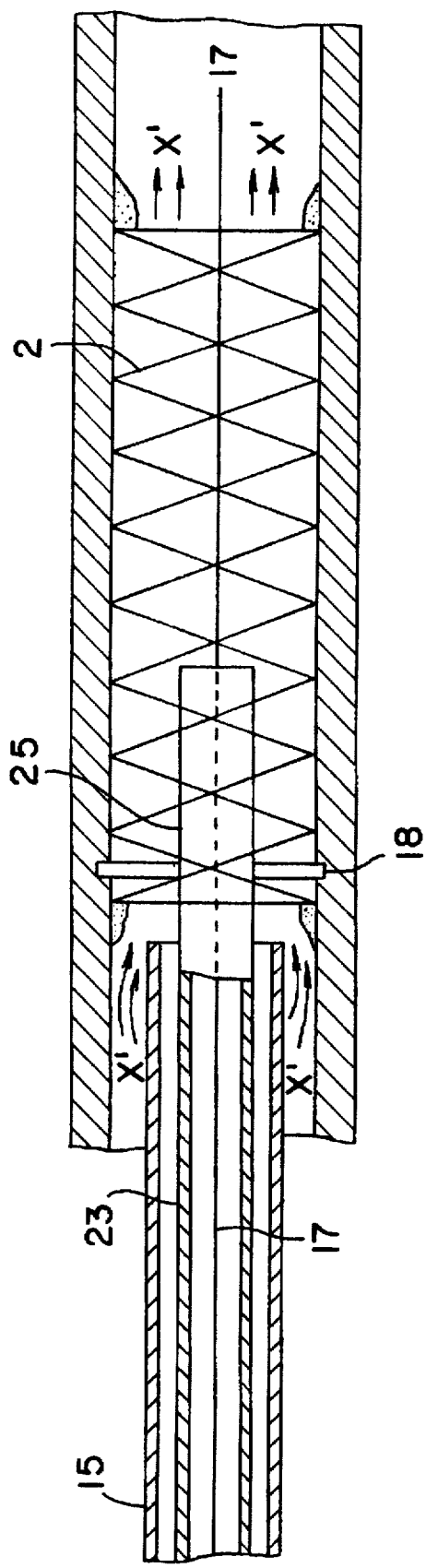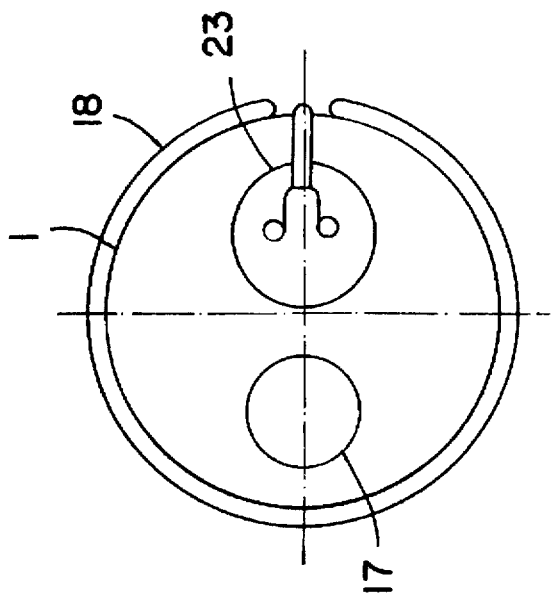

CATHETER WITH EXPANDABLE WIRE MESH TIP

This is a division of application Ser. No. 08/210,195, filed on Mar. 19, 1994, which was a division of application Ser. No. 07/904,793, filed on Jun. 26, 1992, now abandoned.

BACKGROUND OF THE INVENTION

Catheters having inflatable balloons mounted on their distal ends are a commonly used apparatus for entering blood vessels to expand and open strictures at remote sites in a non-invasive manner.

In conventional balloon catheters, vessel expansion is achieved by inflating the balloon on the catheter tip at the site of the obstruction. The balloon expands radially outward, thereby expanding the place in the blood vessel where it is located.

One disadvantage of the conventional balloon catheter is that blood flow through the lumen of the vessel in which the balloon is to be inflated, which is already severely reduced because of the stricture, is momentarily completely cut-off when the balloon is inflated and exerting pressure against the stricture-causing mass and/or wall of the vessel. If such a condition is maintained for an extended period of time it is possible that damage to or necrosis of the tissue material of the vessel wall may occur.

Accurate control of the extent of inflation of the balloon may also be difficult to achieve in some circumstances with conventional balloon catheters. If inflation is not carefully monitored and controlled, it is possible to overinflate the balloon which in turn may cause a stretching and weakening of the vessel wall.

In the particular application of balloon catheters to angioplasty, moreover, there is a possibility, which occurs at a frequency on the order of about 5% of the cases, of the abrupt reclosure of an expanded artery after balloon angioplasty. This is generally due to a dissection of the arterial wall obstructing the lumen, to elastic recoil of the arterial wall, or to spontaneous spasm of the arterial wall.

SUMMARY OF THE INVENTION

Accordingly, a catheter featuring a novel means of lumen expansion at its distal end has been developed. The present invention utilizes an expandable wire mesh tip attached to the distal end of the catheter. In certain embodiments of the catheters, the wire mesh tip is expanded at the situs of a stricture in a lumen through which the catheter is being manipulated by means of a control mechanism which pulls on the mesh to shorten the length of the mesh device while simultaneously expanding its diameter. In certain other embodiments, a wire mesh material with intrinsic shape restoring properties is employed as the material of the wire mesh tip, with the wire mesh tip being fabricated to have a default position in an expanded state, and a moveable sheath being utilized as the means to alternatively contain the wire mesh tip in a contracted position.

A catheter for insertion in the lumen of a vessel according to the present invention generally includes the elements of a tubular catheter body, a wire mesh tip and means for manipulating the wire mesh tip.

The tubular catheter body is of substantially tubular shape, open at both ends, has an inner diameter and an outer diameter, a fixed length, and a proximal end and a distal end.

The wire mesh tip is capable of being configured to have a substantially cylindrical shape of variable dimensions, open at both ends, with the wire mesh tip having a variable diameter, a variable length, and a proximal end and a distal end. The wire mesh tip is attached at its proximal end to the distal end of the catheter body, such that the wire mesh tip and the catheter body are coaxially joined in a lengthwise direction.

The means for manipulating the wire mesh tip is utilized to move the wire mesh tip back and forth between a contracted position, wherein the tip is configured to have dimensions of a contracted diameter substantially equal to and not greater than the inner diameter of the tubular catheter body, and a contracted position length, and at least one expanded position, wherein the tip is configured to have dimensions of an expanded diameter greater than the contracted diameter and not greater than thirty times the outer diameter of the catheter body, and an expanded position length that is shorter than the contracted position length.

BRIEF DESCRIPTION OF THE DRAWINGS

FIG. 1 is a side view of the distal end of one embodiment of a catheter according to the present invention, with a wire mesh tip shown in a contracted position.

FIG. 2 is a side view of the distal end of the catheter of FIG. 1, with the wire mesh tip shown in an expanded position.

FIG. 7 is a side view of an alternative embodiment of a catheter according to the present invention, with a wire mesh tip, shown in a contracted position, and an expansion-contraction control mechanism.

FIG. 8 is a side view of an alternative embodiment of a catheter according to the present invention, with a wire mesh tip, shown in an expanded position, and an expansion-contraction control mechanism, and showing the available flow path.

FIG. 9 is a longitudinal view of the distal end of a catheter according to the present invention with a wire mesh tip further provided with two parallel helical bipolar electrode leads for supplying RF energy to the wire mesh tip.

FIG. 10 is an enlarged view of the distal end of the tubular catheter body and wire mesh tip of FIG. 9 showing details of the path of the two helical bipolar electrode leads through an annular space between the inner and outer walls of the catheter body and attachment of the leads to the wire mesh tip.

FIG. 11 is a side view of an alternative embodiment of a catheter according to the present invention, with a self-expandable wire mesh tip, shown in a constrained position.

FIG. 12 is a side view of the catheter of FIG. 11, with the wire mesh tip shown in an expanded position.

FIG. 13 is a side view of another alternative embodiment of a catheter according to the present invention, with a self-expandable wire mesh tip open at both ends for maximum blood flow.

FIG. 14 is a cross-section view of the catheter of FIG. 13.

DETAILED DESCRIPTION OF THE INVENTION

Figure 3:
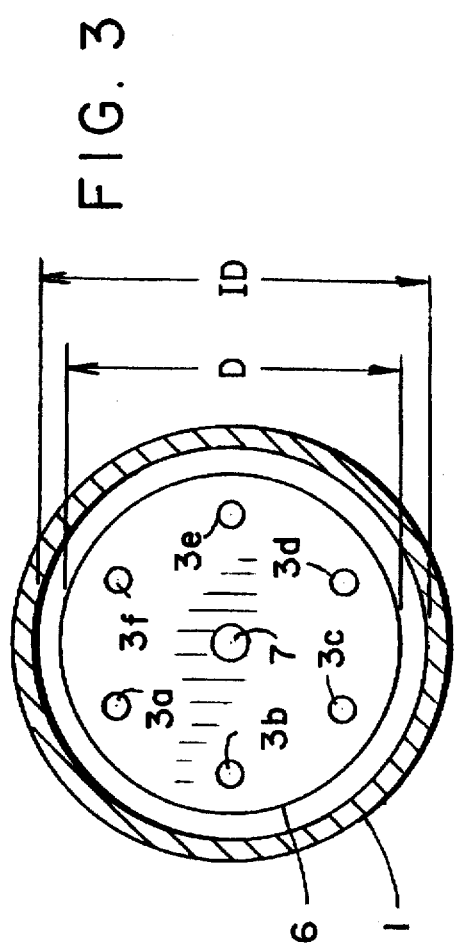
FIG. 3 is an end view of one embodiment of a circular control wire connection plate inside a catheter according to the present invention.

Generally expansion of the wire mesh tip at the end of the catheter is accomplished by compressing the wire mesh tip in a direction along the common longitudinal axis of the tip and the catheter. In certain embodiments of the catheter according to the present invention, this is achieved by actuating an external remote control means which causes a pulling force to be exerted on longitudinal tip control means attached at one end to the leading edge of the wire mesh tip. The control means runs from the points of attachment to the distal end of the wire mesh tip, axially along the length of the wire mesh tip, and then through the tubular body of the catheter to external remote control means to which the opposite end of the tip control means is attached. The tip control means has several alternative embodiments, as will be described, including one embodiment with a plurality of branch control wires attached at one end to the wire mesh and at the other end to one face of an intermediary control plate, with a single main control element attached to an opposite face of the control plate and extending along and out from the catheter, and another embodiment which utilizes only a single main control element attached to the wire mesh by a front plate.

In the embodiment of the apparatus which utilizes a plurality of branch control wires, the tip control means for manipulating the wire mesh tip back and forth between its contracted position and its at least one expanded position generally includes the elements of a plate, a main control element, a plurality of branch control wires, and remote control means.

The plate has a diameter substantially equal to and not greater than the inner diameter of the tubular catheter body. The plate has a front face facing in the direction of the distal end of the catheter body and a back face facing in the direction of the proximal end of the catheter body. In a preferred embodiment, the plate is circular or substantially circular in shape. Alternatively, the plate can be square, rectangular or polygonally shaped, preferably having at least six sides. The plate is oriented in a plane perpendicular to the longitudinal axis of the catheter body, such that a clearance is provided between the plate and the inner diameter of the tubular catheter body to enable movement of the plate back and forth along the longitudinal axis of the catheter body.

The plurality of branch control wires, each having a proximal end and a distal end, are each attached at their distal ends to the distal end of the wire mesh tip at selected points around the circular perimeter of the cylindrically shaped wire mesh tip at the distal end of the tip. The wire mesh tip is preferably open at both ends to enable the maximum possible flow through the wire mesh tip. The branch control wires have a length greater than the length of the wire mesh tip in its contracted position, such that the branch control wires extend longitudinally from their points of attachment at the distal end of the wire mesh tip parallel to the length of the wire mesh tip in a direction toward the proximal end of the catheter body, with each branch control wire being attached at its proximal end to the front face of the plate at selected points on the front face of the plate. When the wire mesh tip is in its contracted position, having its maximum length, the plate is positioned at a first position thereof, and the branch control wires are positioned at a first position thereof, having a maximum component of their length that is parallel to and coaxial with the longitudinal axis of the catheter body. When the wire mesh tip is in an expanded position, the plate is positioned at a second position thereof, wherein the plate extends further toward the proximal end of the catheter body than when the plate is in its first position, and the branch control wires are positioned at a second position thereof, having a component of their length that is parallel to and coaxial with the longitudinal axis of the catheter body, which is shorter than the maximum component when in the first position. Alternative embodiments of the apparatus according to the present invention can incorporate from 2 to 12 branch control wires. A preferred embodiment utilizes six branch control wires.

The main control element having a proximal end and a distal end, is attached at its distal end to the back face of the plate, and extends longitudinally away from the plate through the catheter body, coaxially with the longitudinal axis of the catheter body, in a direction toward the proximal end of the catheter body. The main control element exits from the proximal end of the catheter body and terminates at the proximal end of the main control element. The main control element is a wire or a solid rod of sufficient diameter and rigidity to transmit a pulling force while remaining flexible, and not kinking. Alternatively, a hollow tube can be used as the main control element in place of a wire or solid rod. The maximum diameter of the main control element is less than the inner diameter of the tubular catheter body, so that an annulus remains between the outer wall of the main control element and the inner wall of the tubular catheter body.

The proximal end of the main control element exits at the proximal end of the catheter body, and is attached to the remote control means for enabling remote actuation to cause the wire mesh tip to change its position from its contracted position, in which the wire mesh tip is maintained while the catheter is being deployed in the lumen of a vessel, to its the expanded position, in which the wire mesh tip is maintained while an obstruction in the lumen is compressed against the walls of the lumen to restore circulation through the lumen. The remote control means is also capable, alternatively, of reversible actuation to cause the wire mesh tip to change position from its the expanded position to its contracted position in order to enable withdrawal of the catheter from the lumen.

The wire mesh tip is caused to move from its contracted position to its expanded position by actuating the remote control means in such a way as to exert a pulling force on the proximal end of the main control element causing the main control element to move in a longitudinal direction parallel to the longitudinal axis of the catheter body, towards the proximal end of the catheter body. The pulling force on the main control element is transmitted to the plurality of branch control wires by the plate, causing the plate and the branch control wires to be displaced from their respective first positions to their respective second positions and causing the distal end of the wire mesh tip to be moved from its contracted position to its expanded position.

Conversely, deactuation of the remote control means to terminate the pulling force on the main control element causes the main control element, the plate and the branch control wires to return from their respective second positions to their respective first positions, by moving those elements in a direction towards the distal end of the catheter body, thereby causing the wire mesh tip to return to its contracted position from its expanded position.

Referring to FIG. 1, depicting a preferred embodiment utilizing a plurality of branch control wires, distal end of catheter 1 with wire mesh tip 2 is shown in its contracted position of diameter $D_1$. A plurality of branch control wires 3, three being shown as 3a, b and c, are attached to the leading edge of the mesh 4 around its periphery at connections 5, the three connections shown as 5a, b and c corresponding to the points of connection of the three branch control wires, respectively. The branch control wires 3 are oriented longitudinally with the mesh device and coaxially with the principal longitudinal axis of the overall catheter. The branch control wires 3, have length L, which is longer than the length of the mesh tip 2 in its contracted position $L_1$. The wires extend an initial distance $L_2$ into the annulus of the catheter when the mesh tip is in its contracted position. A total of from 2 to about 12 branch wires 3 may be utilized around the periphery of the wire mesh tip. In one preferred embodiment, a total of 6 branch control wires are utilized, equidistantly spaced around the periphery. The ends of the branch control wires opposite to those attached to the leading edge of the wire mesh tip are attached to an outer, front face of circular plate 6, which has a diameter slightly smaller than the inside diameter of the tubular catheter body. Referring to FIG. 3, one preferred configuration of circular plate 6, accommodating a total of 6 branch control wires 3a–f attached to the wire mesh tip, is shown in end view. The plate 6 has a diameter D which is slightly smaller than the inside diameter (ID) of tubular catheter body 1 to enable free movement of plate 6 axially along the catheter.

A main control wire 7 is attached to the opposite, back face of circular plate 6 and extends therefrom along the length of catheter 1 to a remote control means external to the catheter (not shown) which enables an operator to pull on the main control wire 7. This pulling force is transmitted to the branch control wires 3 attached to the wire mesh tip 2 via the circular plate 6 to which all branch control wires are attached, thereby causing the wire mesh tip 2 to move from its contracted position to an expanded position. Alternatively, control wire 7 is a hollow tube.

Referring to FIG. 2, the distal end of catheter 1 with wire mesh tip 2 attached thereto is shown in its expanded position of diameter $D_2$. Main control wire 7 has been pulled in the direction of arrow W axially through the annulus of the tubular catheter body away from the distal end of the catheter. This causes circular plate 6 to which control wire 7 and all branch control wires 3 are attached to move from position X shown in FIG. 1 to position Y shown in FIG. 2. In this expanded position, the portion of the total length L of branch control wires 3 in the annulus of the catheter changes from $L_2$, shown in FIG. 1 for the contracted position to $L'_2$ for the expanded position of FIG. 2. At the same time, the length of the wire mesh tip and hence the portion of the length of branch control wires 3 therein is shortened from $L_1$ shown in FIG. 1 for the contracted position, to $L'_1$ shown in FIG. 2 for the expanded position. The expansion of wire mesh tip 2 on the distal end of catheter 1 from its contracted position shown in FIG. 1, in which condition it is emplaced in the lumen of a vessel, to its expanded position shown in FIG. 2, causes an increase in the effective passageway in the lumen of the vessel available for blood flow of width $D_2-D_1$, where $D_2$ is the diameter of an unconstricted vessel and $D_1$ is the diameter of a vessel with a stricture. Expansion of the wire mesh device at the stricture will cause a pliable stricture-causing material, such as plaque, to be compressed at the walls of the vessel and open the passageway by a width $\Delta D=D_2-D_1$, for improved flow.

The wire mesh tip on the distal end of the catheter, once having been expanded according to the foregoing, is again fully retractable to its initial position, wherein the catheter and tip can be withdrawn from the vessel. Reconfiguration of the wire mesh tip to its contracted position is accomplished by a reversal of the procedure used to expand the tip. The operator deactuates the external remote control means which removes the pulling force exerted on the control wire means and associated elements.

The catheter with wire mesh tip at its distal end, according to the present invention, has several advantages over conventional balloon catheters.

The catheter with wire mesh tip allows precise control of the diameter to which the mesh is expanded, thereby eliminating the possibility of over-expansion and possible consequent damage to the vessel.

Another advantage of the catheter and wire mesh tip system of the present invention is that the system does not totally occlude the blood vessel when the wire mesh tip is expanded. Even in its fully expanded state, blood will continue to flow through the open ended, generally cylindrically-shaped wire mesh tip along a flow path from the outer wall of the catheter to the edge of the wire mesh tip.

Figure 4:
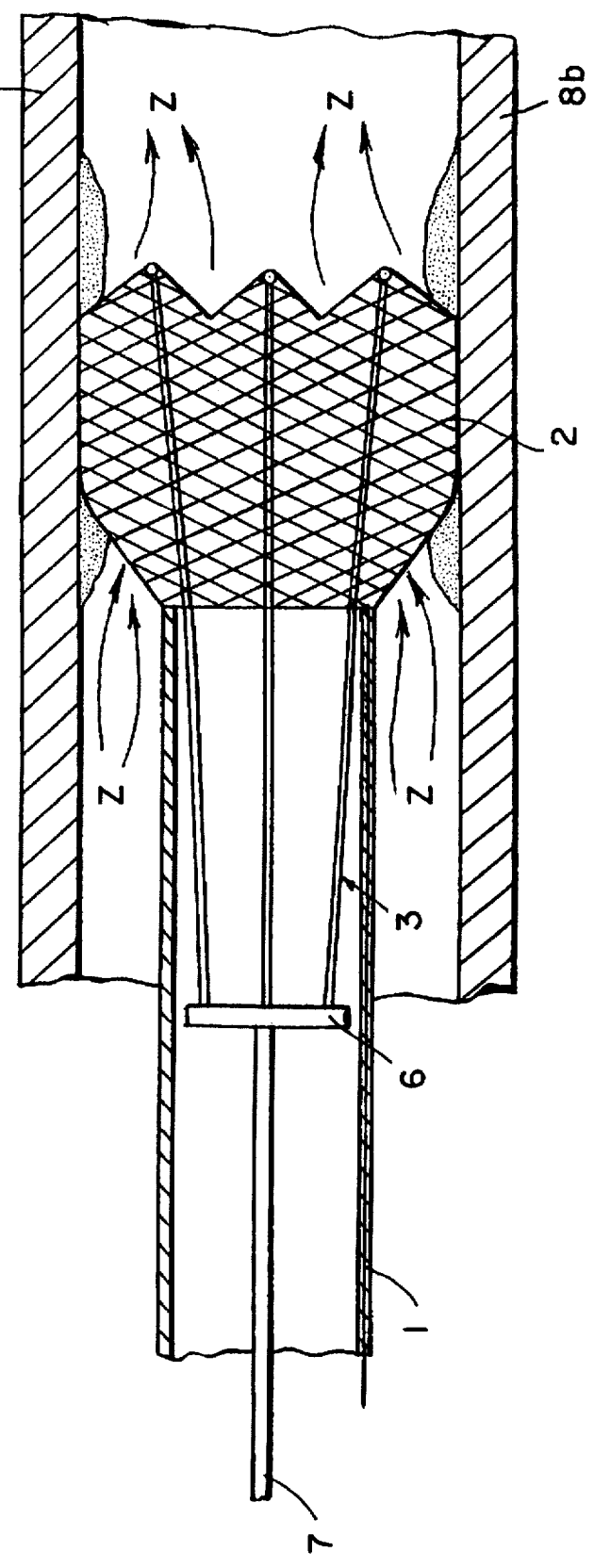
FIG. 4 is a side view of a catheter according to the present invention, with a wire mesh tip in an expanded position inside a vessel, and showing the available flow path.

FIG. 4 shows catheter 1 with wire mesh tip 2 in its expanded position in place in a vessel whose walls are shown in side view by 8a, b. The arrows designated z define the flow path through the blood or fluid permeable mesh even when the mesh device is in its expanded position.

The wire mesh tip of a catheter according to the present invention can be fabricated from any type of wire mesh material with a mesh size that has sufficient permeability to allow the flow of blood or whatever fluid is flowing through the vessel in which the catheter is being utilized through the mesh when the tip is in its expanded position, in order that the lumen in which the catheter is being manipulated does not become totally occluded to flow when the mesh tip is in expanded position.

The wire mesh material itself can be fabricated from any biologically inert material. It is preferable that the wire be metal, although certain inert plastics having sufficient strength may also be used. Stainless steel, titanium, titanium alloy, nitinol (nickel-titanium alloy), and vitallium alloy are suitable metallic materials of construction of the wire mesh. High molecular weigh polyethylene is a suitable plastic material of construction.

The wire mesh material can be made in a variety of patterns. Braided, woven and knit designs can be utilized as long as the fineness of the mesh size is greater than the molecular size of the fluid to be transmitted therethrough, so that fluid flow is not prevented by the mesh.

The extent of compression of the flow obstructing material in the vessel that is effected by expansion of the wire mesh tip is determined in part by the fineness of the mesh material and the pattern that it forms which is utilized. Thus, if a tightly woven mesh is used, the flow obstructing material will be fairly evenly compressed against the wall of the vessel, whereas if a more loosely woven wire mesh is utilized, compression of the flow obstructing material against the wall of the vessel will occur only where the mesh comes in contact with the material. There will be little or no compression in the interstices between the mesh. In this case, a waffle pattern will be impressed on the flow obstructing material. If the mesh material is sharp, it may cut into the flow obstructing mass causing particles of it to be cut away.

Rather than having particles of the flow obstructing material become cut loose or abrade from the vessel wall and be free to circulate through the vessel, it is instead, desirable to either weld the material in a compressed state to the vessel wall or ablate the material. This is accomplished by provision for alternative means for welding or ablating the material, such as through the application of radio frequency energy to the material, as is described in detail below.

The wire mesh tip expansion-contraction controlling mechanism of the apparatus of the present invention can also be fabricated in a variety of alternative ways to the main control element-plate-branch control wires combination of the embodiment discussed above. According to such alternative embodiments of the catheter, which also generally include a catheter body, a wire mesh tip and means for manipulating the wire mesh tip, the means for manipulating said wire mesh tip back and forth between its contracted position and its at least one expanded position includes a substantially circular element having a diameter substantially equal to and not greater than the inner diameter of the tubular catheter body and having a front face facing in the direction of the distal end of the catheter body and a back face facing in the direction of the proximal end of the catheter body. The element is oriented in a plane perpendicular to the longitudinal axis of the catheter body, and is attached to the wire mesh tip around the circular perimeter of the cylindrically shaped wire mesh tip at the distal end of the wire mesh tip. The substantially circular element attached to the leading edge of the open cylindrical wire mesh tip around the periphery thereof according to these alternative embodiments, is alternatively, an element selected from the group consisting of an annular ring, a solid circular plate, and a perforated circular plate.

These embodiments also include a control element, which alternatively is a wire, a solid rod or a hollow tube, having a proximal end and a distal end, attached at its distal end to the back face of the substantially circular element and extending longitudinally away from the element through the catheter body, coaxially with the longitudinal axis of the catheter body, in a direction toward the proximal end of the catheter body, and terminating at the proximal end of the element, exiting from the proximal end of the catheter body. The maximum diameter of the control element is less than the inner diameter of the tubular catheter body, leaving an annulus between the control element and the inner wall of the tubular catheter body. When the circular element is an annular ring, the mechanism for manipulating the wire mesh tip further includes a plurality of supporting struts for attaching the control element to the annular ring. One end of each of the plurality of supporting struts is attached to a solid outer portion of the annular ring around the periphery thereof, and the opposite end of each of the plurality of said supporting struts is attached to the control element. In one preferred arrangement, the plurality of supporting struts are oriented co-planar with the annular ring and the distal end of the control element, and in an alternative preferred arrangement, they have a portion of their length non-coplanar with the annular ring, which portion of their length extends axially with the control element in a direction towards the proximal end thereof. Alternative embodiments of the control mechanism of this embodiment of catheter according to the present invention can have from 2 to 12 supporting struts. A preferred embodiment has from 3 to 8 supporting struts.

When the circular element is an element selected from a solid plate and a perforated plate, the catheter further includes a plurality of supporting struts each attached at one end thereof to the circular element around its periphery, and at an opposite end of each of the plurality of supporting struts to the control wire, such that the supporting struts have a portion of their length extending axially with the control element in a direction towards the proximal end thereof.

Finally, the wire mesh tip manipulating means for these alternative embodiments also includes remote control means to which the proximal end of the control element is attached, for enabling remote actuation to cause the wire mesh tip to move from its contracted position, alternatively to an intermediate partially expanded position or to the fully expanded position at which an obstruction in the lumen of the vessel in which the catheter is deployed is compressible against walls of said lumen in order to restore circulation through said lumen. The remote control means is also utilized to later cause the wire mesh tip to return to its initial contracted position to enable withdrawal of said catheter from the lumen.

FIGS. 5, 6, 7 and 8 show elements of the foregoing alternative wire mesh tip control mechanisms and their employment.

Figure 5A:
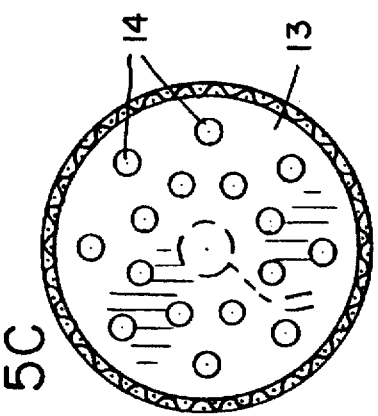
FIGS. 5a, b and c are front end views of alternative embodiments of elements of the wire mesh tip expansion-contraction control mechanism according to the present invention.
Figure 6A:
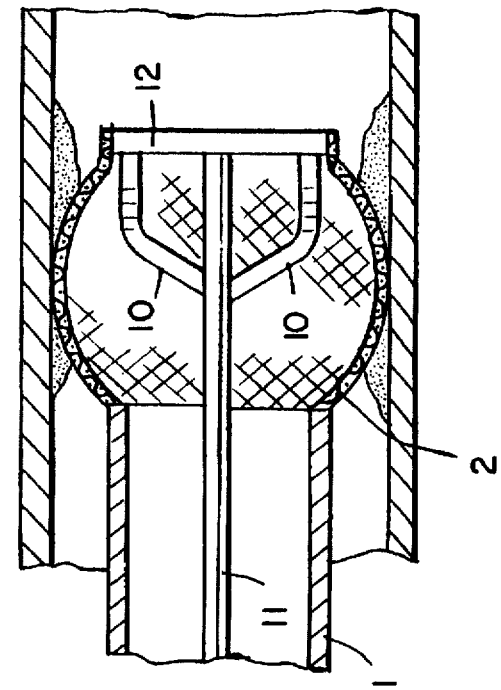
FIGS. 6a and b are side views of alternative embodiments of the wire mesh tip expansion-contraction control mechanism according to the present invention.

In one alternative embodiment of the control mechanism shown in FIG. 5a, an annular ring 9 is utilized. Annular ring 9 is attached to the leading edge of the periphery of wire mesh tip 2, shown in FIG. 6. A main control wire 11 is utilized to move the ring in a longitudinal direction along the axis of the tip and catheter to cause the wire mesh tip to move from its contracted position to an expanded position and back. Control wire 11 is attached to annular ring 9 by a plurality of supporting struts 10 which are attached at one of their ends to the edge of the ring and at their opposite end to control wire 11. FIG. 5a shows one example of such an annular ring control mechanism having four struts 10a–d equidistantly distributed around the perimeter of the annular ring 11, by which the ring 11 is attached to main control wire 11. The supporting struts 10 can be positioned such that they are within the plane of the ring 9, or they may have a portion extending parallel to or at an angle with their point of attachment to control wire 11 to their point of attachment to the ring 9, such that the points of attachment to ring and control wire are in different planes perpendicular to the axial direction of the catheter as shown in FIG. 6a. The annulus of ring 9 is an additional path available for blood or fluid flow when the wire mesh tip is in an expanded position, as shown by arrows X in FIG. 8.

Figure 5B:
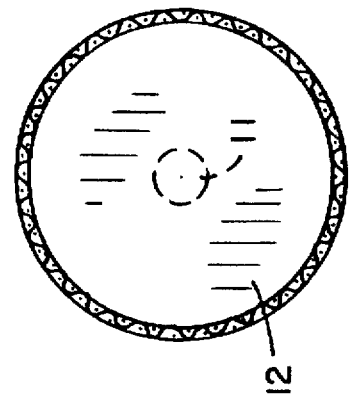
Figure 6B:
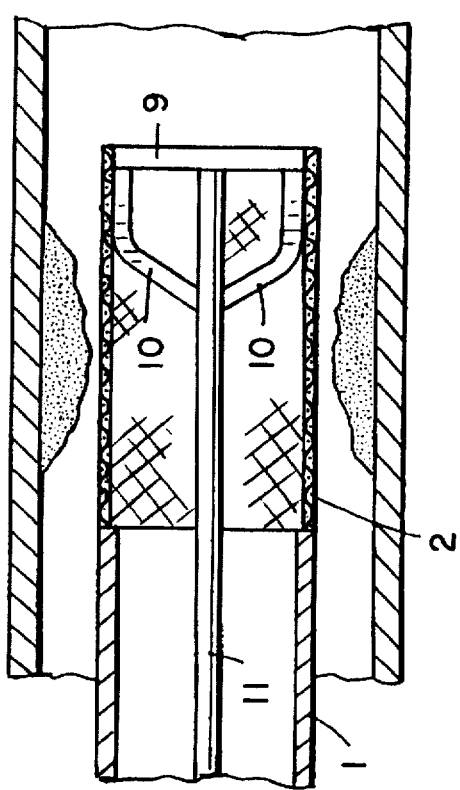

Other alternative embodiments of the control mechanism, utilizing a solid circular plate and a perforated plate, respectively, are shown in FIGS. 5b and c. The solid circular plate element 12 of FIG. 5b is also attached to the leading edge of the wire mesh tip around its periphery, but allows for direct attachment of control wire 11 to the rear face of the plate. Circular plate 12 can be more securely attached to control wire 11 by the use of a plurality of reinforcing struts 10 distributed around the periphery of the plate with one end attached thereto and the other end attached to control wire 11, as shown in FIG. 6b. The solid circular control plate 12 does not present additional flow path area for fluid flow. Where such a control element is utilized, the flow path for fluid flow with the mesh tip in an expanded position is limited to flow channels through the wire mesh itself, as shown by arrows z in FIG. 8.

Figure 5C:
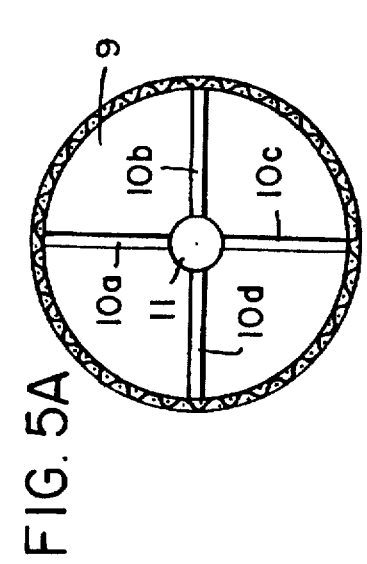

Another alternative embodiment of the control mechanism utilizes a perforated disk, as shown in FIG. 5c. The perforated disk 13 embodiment of the control element offers the advantage of a more solid point for attachment of control wire 11, as with the solid circular plate embodiment 12, while allowing for additional channels for fluid flow through the perforations, when the mesh tip is in the expanded position, shown by arrows X in FIG. 8, as with the annular ring element.

In certain alternative embodiments of the catheter according to the present invention, the wire mesh tip is fabricated from a wire mesh material having intrinsic shape-restoring properties, with the wire mesh tip being fabricated to have a default position in its expanded position. In such an embodiment, the tip is maintained in a contracted state by a sheath which in a first position surrounds the tip and exerts a restraining force which holds the wire mesh together. When it is desired to expand the tip, the sheath is retracted to a second position by moving it in a direction toward the proximal end of the catheter body such that it no longer surrounds the wire mesh tip, thereby causing the wire mesh tip to expand without the need for the use of further control means, due to the nature of the material of the wire mesh tip and its having been fabricated in such a manner that a default position of the wire mesh tip, when no external restraining forces are applied to it, is in its expanded position. The sheath in these embodiments essentially corresponds to the tubular catheter body of the previously described embodiments. The wire mesh tip is returnable to its contracted position when the sheath is moved in a direction toward the distal end of the catheter body, into the sheath's first position, wherein it again surrounds the wire mesh tip and exerts a restraining force thereupon, causing the wire mesh tip to remain in its contracted position while the restraining force is exerted by the sheath The proximal end of the wire mesh tip is attached to a control element, which depending upon the application of use of the catheter, is alternatively a rod, a tube or an open coil.

Referring to FIGS. 11 and 12, which illustrate this alternative embodiment, the wire mesh of wire mesh tip 2 is bonded to open coil 23 along a segment of the length of the coil at a point 25. A recovery tube or sheath 15 is used to guide the catheter into position over a guidewire 17. In FIG. 11, the wire mesh tip 2 is shown in the contracted position with the sheath in place; while in FIG. 12, the wire mesh tip 2 is shown in the expanded position, the sheath 15 having been retracted to allow the shape-restoring wire mesh material to expand and deploy the wire mesh tip 2; the flow path for fluid flow with the mesh tip in the expanded position is limited to flow channels through the wire mesh itself, as shown by arrows z' in FIG. 12. The wire mesh tip is fabricated in such a way that its expanded position is the default position when unconstrained, due to the shape-restoring properties of the material, which causes the tip to assume that configuration when the restraining sheath is retracted.

In another alternative embodiment of a wire mesh tipped catheter according to the present invention, which also utilizes a material for the wire mesh, which has intrinsic shape-restoring properties, and the wire mesh tip is fabricated to have a default position in its expanded position, the catheter also includes a control element, which is alternatively a rod, a tube or an open coil as in the above embodiment, which cooperates with the wire mesh tip, and can be alternatively either attached or unattached thereto and also includes as the means for manipulating the wire mesh tip, a string passed through the open coil, with a portion of the string being woven through the wire mesh tip, such that in order to cause the wire mesh tip to assume its contracted position, the string is pulled in a direction toward the proximal end of the catheter and inside the open coil, thereby causing that portion of the string woven through the wire mesh tip to shorten, and in turn, causing the wire mesh tip to partially contract. This alternative embodiment of the catheter also utilizes the movable outer sheath, as described above, which corresponds essentially to the tubular catheter body of previously described embodiments incorporating the control element-plate mechanism for manipulating the wire mesh tip. The sheath is capable of surrounding the wire mesh tip, and has a first position, in which the movable outer sheath surrounds the wire mesh tip, and a second position, in which the movable outer sheath does not surround the wire mesh tip, such that upon manipulation of the movable outer sheath in a direction toward the distal end of the catheter, from the second position to the first position of the outer sheath, a remaining uncontracted portion of wire mesh tip is caused to contract further such that the wire mesh tip is movable to its expanded position, first by manipulation of the outer sheath in a direction toward the proximal end of the catheter, from the first position to the second position of the outer sheath, to partially expand the wire mesh tip, by releasing the distal end of the wire mesh tip, and subsequently releasing the string, allowing the intrinsic shape-restoring force of the wire mesh tip to fully expand the proximal end of the wire mesh tip.

Referring to FIGS. 13 and 14, which illustrate this embodiment, the wire mesh of wire mesh tip 2 is bonded to an open coil 23 at a single connection point 25. A "purse string" 18 is inside of the coil and is woven through the wire mesh tip. The diameter of the wire mesh tip is reduced prior to reinserting the tip in the sheath 15 by retracting or pulling back on the purse string in order to contract the wire mesh tip for recovery and removal from the vessel in which it has been deployed. The flow path for fluid flow with the mesh tip in the expanded position is limited to flow channels as shown by X' in FIG. 13. This embodiment is shown in cross section in FIG. 14.

The wire mesh tip of all embodiments of catheter according to the present invention which utilize a control element-plate type mechanism for manipulating the wire mesh tip are capable of being configured in a number of positions, from fully contracted, through intermediate positions of partial expansion, to a fully expanded position. In each of the plurality of intermediate positions of partial expansion between the fully contracted position and the fully expanded position, the diameter of the wire mesh tip is greater than its diameter in the fully contracted position, less than the maximum diameter in its fully expanded position, and not greater than its maximum diameter of thirty times the outer diameter of the tubular catheter body. The length of the wire mesh tip extending parallel to the axial direction of said catheter body in an intermediate position is shorter than its length in the contracted position, and greater than its length in its fully expanded position.

For all such embodiments, the wire mesh tip is alternatively configurable from its fully contracted position through selected intermediate positions to its fully expanded position; from its fully expanded position through selected intermediate positions to its fully contracted position; from a first selected intermediate position to another selected intermediate position which is alternatively more expanded or more contracted than the first intermediate position, or from an intermediate position to the fully contracted or fully expanded position.

The position and state of configuration of the wire mesh tip with respect to its expansion or contraction is proportional to the pulling force being exerted on the main control wire through the remote control means.

In the embodiments which utilize a wire mesh tip fabricated from an intrinsic shape-restoring material, and utilizing only a movable sheath to deploy the wire mesh tip, the wire mesh tip is only a bipositional device, capable of assuming alternatively only a fully contracted or a fully expanded position. The embodiments of the apparatus which utilize a wire mesh tip fabricated from an intrinsic shape-restoring material, and which further include a pursestring or drawstring as an additional means of control, are capable of assuming a plurality of partially expanded positions between the fully contracted and fully expanded positions, by the exertion of a pulling force on the drawstring to limit the expansion of the wire mesh tip.

For all the embodiments of the wire mesh tip according to the present invention, the wire mesh tip is alternatively fabricated from a single piece of wire mesh which can be joined lengthwise side edge to side edge forming a seam in order to form an open cylindrical tip, or the wire mesh tip can be formed from a plurality of rectangular wire mesh panels, with each panel having a proximal end, a distal end and two sides, the sides being longer than the ends, further with each panel terminating in a forward section having an outwardly facing curvilinear edge, and each panel being longitudinally attached to an adjoining panel on both sides, to form a substantially cylindrical tip. In the embodiments of the apparatus which utilize a main control element-plate-branch control wires system as the means for manipulating the wire mesh tip, alternatively, all or selected ones of the panels have one of the plurality of branch control wires attached thereto, at their forward section.

According to the present invention, the wire mesh material of the wire mesh tip is fabricated in a braided, woven or knot pattern. The wire mesh material of the wire mesh tip has a mesh size that is permeable to the flow of fluid present in the lumen of the vessel in which the catheter is deployed. The wire mesh of the wire mesh tip is fabricated from a metal or plastic that is inert to fluid present in the lumen of the vessel in which the catheter is deployed. Such materials include stainless steel, nitinol, titanium, vitallium and polyethylene.

Depending on the pliability and compressibility of the flow obstructing mass, a vessel in which the effective passageway available for blood flow has been increased by the above procedure may maintain its widened diameter or it may gradually or even acutely return to a stenosed state. In the former case, this occurs by the redeposition of flow obstructing material such as plaque on the walls of the vessel at the same location using the compressed material as a nucleation site for new deposition, or in the latter case by the sudden re-expansion of the compressed mass of material to at or near its original vessel occluding diameter. Occurrence of the latter is particularly undesirable, as it may precipitate acute cardiovascular, particularly coronary, insufficiency resulting in a serious, possibly life-threatening, cardiovascular incident, manifested as a heart attack or stroke.

In order to prevent the re-occurrence of either type of occlusive condition, it is desirable that the flow obstructing material be removed rather than merely compressed.

It is known that radio frequency (RF) energy is effective in cutting or ablating plaque deposits on blood vessel walls, and for coagulating tissue.

Accordingly, certain embodiments of a wire mesh tipped catheter according to the present invention further include a wire for transmitting radio frequency energy. The wire extends the length of the tubular catheter body from the proximal end thereof to the distal end thereof. The wire is positioned in the annulus formed between the outer diameter of the inner tubular wall and the inner diameter of the outer tubular wall of the tubular catheter body, the wire being connected at a distal end thereof to the wire mesh tip.

A source for generating radio frequency energy connected to the wire at a proximal end thereof, external to the proximal end of the tubular catheter body is also provided.

In one embodiment, the wire for transmitting radio frequency energy is a main transmitting wire which is connected to the wire mesh tip at a plurality of points of attachment on the outer surface of the wire mesh through a corresponding number of branch transmitting wires extending from the main transmitting wire to the points of attachment.

For embodiments of catheters according to the present invention which utilize a plurality of branch control wires and a plate as part of the means for manipulating the wire mesh tip, radio frequency energy is delivered in one embodiment by means of an ablation electrode attached to the plate and insulated from the wire mesh tip. In these embodiments, a hollow tube is preferably utilized as the main control element to provide an annulus between the outer wall of the tubular control element and the inner wall of the tubular catheter body in which the wire for transmitting electrical energy is placed to insulate it from the inner lumen of the tubular control wire. The inner lumen of the tubular control wire also provides a convenient lumen through which suctioning of debris and fluids can be performed. This embodiment also includes a wire for transmitting electrical energy to the electrode. The wire extends through the length of the wire mesh tip, and is insulated therefrom. It further extends through the length of the tubular catheter body from the proximal end thereof to the distal end thereof, and is insulated from the wire for transmitting radio frequency energy to the wire mesh tip, which is also contained in the annulus. Also included is a source for generating electrical energy for the ablation electrode, which is connected to the wire for transmitting electrical energy at the proximal end of the wire, external to the proximal end of the wire which is external to the proximal end of the tubular catheter body.

Referring to FIG. 9, a conducting wire 8 for supplying RF energy to all or a portion of the mesh tip is shown. The wire 8 is positioned in the annulus formed between the inner wall of the tubular catheter body and the outer wall of a tubular control wire, running axially along the length of the catheter from its proximal end, at which it is connected to a source of RF energy, to the distal end of the catheter, which interfaces with the proximal end of the wire mesh tip, and where the conducting wire is connected to the wire mesh tip at one location, or through a plurality of branching conducting wires (not shown), to a plurality of locations on the outer surface of the open cylindrical wire mesh tip.

The RF energy transmitting wire electrodes attached to the wire mesh tip can be either monopolar or bipolar.

Bipolar electrodes can be utilized with a braided wire mesh by running two leads to two parallel helical elements in the mesh and insulating all other members from those two members, by fabricating all other members of the braided mesh from electrically non-conducting material such as plastic or by providing insulation over the otherwise electrically conductive wires to make them non-conducting. The two parallel helical members should both be either right hand or left hand helixes so that their elements do not cross.

FIG. 9 shows how two parallel helical RF energy transmitting electrode leads 8a, b do not cross when attached to braided wire mesh tip 2.

FIG. 10 shows an expanded view of the distal end of catheter 1 showing the double wall tubular construction formed by the inner wall of the tubular catheter body, and the outer wall of a tubular control wire, and wire mesh tip 2 attached, with two RF transmitting leads 8a, b of a bipolar electrode running through the annular space between the inner and outer walls of the tubular catheter body and attached to the wire mesh tip as parallel helixes not in contact with one another.

An advantage of the embodiment of the catheter with wire mesh tip, further provided with an RF energy transmitting electrode attached to the mesh tip, is that it allows the RF energy to be transmitted through all or part of the mesh to cut, ablate or coagulate tissue.

For angioplasty applications, this allows for the capability of first expanding the mesh tip to compress the restrictive plaque or other mass and then coagulate to seal it in its compressed position to prevent its reexpansion and the restenosis of the vessel.

In the treatment of benign hypertrophy of the prostate, the system of the present invention with RF energy transmission capability can be utilized in a cutting mode to first expand the mesh tip and then rotate it while applying RF energy to the expanded mesh to cut out a plug of tissue to remove the urethral stricture.

The apparatus of the present invention, particularly the embodiment incorporating means for applying RF energy to the surrounding tissue can also be utilized in the treatment of percutaneous diskectomy, wherein the expanded wire mesh tip is first used to entrap tissue which is then ablated or cut with the RF energy.

Catheters utilizing alternative wire mesh tip actuation control means incorporating an annular ring 9, solid disk 12 or perforated disk 13 can be provided with bipolar or sesquipolar electrodes by using one or more wires of the mesh tip 2 as one electrode and the ring 9 or disk 12, 13 as the other electrode. The ring 9 or disk 12, 13 must be insulated from the wire mesh 2. Separate RF energy supplying leads are connected to the wire mesh 2 and to the ring 9 or disk 12, 13.

In such a configuration, the electrode connected to the front ring 9 or disk 12, 13 can function as an ablation electrode, while the electrode connected to the wire mesh tip is utilized for coagulation or welding plaque to the wall of the vessel.

For all of the embodiments of the catheter of the present invention, it has been found that the possibility of the occurrence of a thrombosis can be reduced by coating all or part of the catheter and the elements thereof which come in contact with blood in a lumen of a vessel with a non-thrombogenic material, such as heparin or hirudin.

For all applications, the elements of the catheter, and particularly the wire mesh tip can also be coated with an elastomeric material to facilitate movement of the catheter through the lumen by decreasing any tendency to adhere to the lumen wall. The preferred elastomeric materials include silicone and thermoplastic elastomers, such as extruded and injection-molded elastomers, and particularly polyurethane and polyethylene.

It has also been found useful in the method of use of the catheter to prime it with one or more of a radiopaque solution to assist in placement of the catheter by monitoring it with an instrument capable of detecting a change in electromagnetic wave penetration; and a saline solution to give the outer surface of said catheter a blood pH compatible coating.

The method of use of catheters according to the present invention in procedures to remove a mass obstructing the lumen of a vessel to increase flow through the lumen, such as in angioplasty for the removal of plaque, in the treatment of benign hypertrophy of the prostate to remove prostatic tissue causing a urethral stricture, and in the treatment of percutaneous diskectomy to remove tissue, generally includes the steps of inserting the catheter with the wire mesh tip in a contracted position into the lumen of the vessel; advancing the catheter to the situs of the obstruction; expanding the wire mesh tip of the catheter to compress the obstruction and open the lumen for increased flow therethrough; maintaining the wire mesh tip in the expanded position for a sufficient time to maintain the obstruction in a compressed state so that it will remain compressed after the catheter is withdrawn; optionally utilizing electromagnetic energy such as radio frequency energy to ablate the obstruction; re-contracting the wire mesh tip; and withdrawing the catheter from the lumen.

The specific method utilized with catheters according to the present invention, the embodiments of which are as illustrated in FIGS. 1–10, is described by the following procedure.

The catheter, having a flexible tubular body and a flexible open cylindrical wire mesh tip attached at a proximal end thereof to a distal end of the tubular catheter body, with the wire mesh tip being in an initial contracted position wherein the wire mesh tip is configured to have dimensions of a contracted diameter approximately equal to the inner diameter of the tubular catheter body and a contracted position length is first inserted into the lumen of the vessel to be cleared of an obstruction.

The catheter is then advanced through the lumen so that the wire mesh tip is positioned at the situs of the flow obstruction.

Remote control means external to the catheter and connected to the wire mesh tip by a control wire and associated means are then actuated to cause the wire mesh tip to be reconfigured to an expanded position at the situs of the flow obstruction, such that the wire mesh tip has an expanded diameter greater than its contracted diameter and not greater than thirty times the outer diameter of the outer wall of the tubular catheter body and a length equal to an expanded length in the axial direction of the tubular catheter body that is shorter than the contracted length. The expansion of the diameter of the wire mesh tip at the situs of the flow obstruction produces a compression of flow obstructing material against the tubular wall of the lumen to widen the passageway for flow through the lumen.

Optionally, radio frequency energy supplied from a source external to the catheter and transmitted through at least one transmitting wire to the wire mesh tip to which a distal end of said at least one transmitting wire is attached, is utilized to energize the wire mesh tip to cut or ablate the flow obstructing material with which the wire mesh tip is in contact while in its expanded position.

Suction through the catheter is also optionally utilized to remove any debris formed during cutting or ablation.

The remote control means is then deactuated to cause the wire mesh tip to be restored to its the first contracted position.

Finally, the catheter is withdrawn from the lumen.

The specific method utilized with catheters according to the present invention, the embodiment of which is illustrated in FIGS. 11–12, is described by the following procedure.

The catheter is first inserted into the lumen of the vessel to be cleared of an obstruction. The wire mesh tip is fabricated from a wire mesh material having intrinsic shape-restoring properties, with the wire mesh tip being fabricated to have a default position in an expanded position thereof, such that the wire mesh tip is initially in a contracted position wherein the tip is configured to have dimensions of a contracted diameter substantially equal to and not greater than the inner diameter of the tubular catheter body and a contracted position length. The wire mesh tip is bonded to an open coil which acts as a control means. In the embodiment, moreover, the tubular catheter body is slidable with respect to the wire mesh tip and acts as means for manipulating the wire mesh tip, by functioning as a movable outer sheath for the wire mesh tip. The sheath (tubular catheter body), which in a first position surrounds the wire mesh tip in its contracted position, exerts a restraining force on the wire mesh tip against expansion thereof to its default position, such that when the sheath is moved in a direction toward the proximal end of the catheter body from its the first position to a second position, wherein it no longer surrounds the wire mesh tip, the wire mesh tip is caused to expand to its said expanded position, due to the removal of said restraining force of the sheath on the wire mesh tip and the shape-restoring properties of the material of the wire mesh tip, which cause the wire mesh tip to expand in the absence of the restraining force from the sheath.

The catheter is then advanced through the lumen so that the wire mesh tip is at the situs of the flow obstruction.

The movable outer sheath (tubular catheter body) is then moved to its second position to cause the wire mesh tip to expand at the situs of the flow obstruction, such that the wire mesh tip has an expanded diameter greater than its contracted diameter and less than thirty times the outer diameter of the tubular catheter body and an expanded position length in the axial direction of the tubular catheter body that is shorter than the contracted position length. Expansion of the diameter of the wire mesh tip at the situs of the flow obstruction produces a compression of the flow obstructing material against the tubular wall of the lumen to widen the passageway for flow through the lumen.

Optionally, radio frequency energy supplied from a source external to the catheter and transmitted through at least one transmitting wire to the wire mesh tip to which the distal end of the at least one transmitting wire is attached, is utilized to energize the wire mesh tip to cut or ablate the flow obstructing material with which the wire mesh tip in its expanded position is in contact.

Suction through the catheter is also optionally utilized to remove any debris formed during cutting or ablation.

The wire mesh tip is returnable to its contracted position when the sheath is moved in a direction toward the distal end of the catheter body to its first position, wherein it again surrounds the wire mesh tip and exerts a restraining force thereupon, causing the wire mesh tip to remain contracted while the restraining force is exerted thereon by the sheath.

The movable outer sheath (tubular catheter body) is then moved to its first position to cause the wire mesh tip to be restored to its first, contracted position.

Finally, the catheter is withdrawn from the lumen.

The specific method utilized with catheters according to the present invention, the embodiment of which is illustrated in FIGS. 13–14, is described by the following procedure.

The catheter is first inserted into the lumen of the vessel to be cleared of an obstruction. The wire mesh tip is fabricated from a wire mesh material having intrinsic shape-restoring properties, with the wire mesh tip being fabricated to have a default position in a second, expanded position thereof. The wire mesh tip cooperates with an open coil, such that the wire mesh tip is initially in a first contracted position wherein the wire mesh tip is configured to have dimensions of a contracted diameter substantially equal to and not greater than the outer diameter of the outer tubular wall of the tubular catheter body, and a contracted position length. In this embodiment, moreover, the tubular catheter body acts as means for manipulating the wire mesh tip between its first and second positions, by functioning as a sheath for the wire mesh tip. The sheath has a first position in which it surrounds the wire mesh tip, and a second position in which it does not surround the wire mesh tip. The wire mesh tip manipulating means further includes a string which passes through the open coil, with a portion of the string being woven through the wire mesh tip, such that in order to cause the wire mesh tip to move from its first position to its second position, the outer sheath is first moved from its first position to its second position, to release the distal end of the wire mesh tip. The string is subsequently released to allow the intrinsic shape-restoring properties of the wire mesh tip to cause the proximal end of the wire mesh tip to fully expand. To cause the wire mesh tip to move from its second position to its first position, the string is first pulled in a direction toward the proximal end of the catheter, to thereby shorten the portion of the string woven through the wire mesh tip, partially contracting the wire mesh tip, and subsequently moving the outer sheath in a direction toward the distal end of the catheter, to move the outer sheath into its first position wherein it surrounds the wire mesh tip, thereby fully contracting the wire mesh tip.

The catheter is then advanced through the lumen so that the wire mesh tip is at the situs of the flow obstruction.

The movable outer sheath (tubular catheter body) is then moved proximally to its second position and the string is released to cause the wire mesh tip to expand at the situs of the flow obstruction, such that the wire mesh tip has an expanded diameter greater than its contracted diameter and less than thirty times the outer diameter of the outer tubular wall of said catheter, and an expanded position length extending parallel to the axial direction of the catheter that is shorter than the first position length. Expansion of the diameter of the wire mesh tip at the situs of the flow obstruction produces a compression of flow obstructing material against the tubular wall of the lumen to widen the passageway for flow through the lumen.

Optionally, radio frequency energy supplied from a source external to the catheter and transmitted through at least one transmitting wire to the wire mesh tip to which the distal end of the at least one transmitting wire is attached, is then utilized to energize the wire mesh tip to cut or ablate the flow obstructing material with which the wire mesh tip in its expanded position is in contact.

Suction through the catheter is also optionally utilized to remove any debris formed during cutting or ablation.

The movable outer sheath (tubular catheter body) is then moved to its first position to cause the wire mesh tip to be restored to its first, contracted position.

Finally, the catheter is withdrawn from the lumen.

According to the method of use of the apparatus of the present invention, an embodiment of a catheter of the present invention is left in place in the lumen of a vessel to compress an obstruction therein and enlarge the flow path through the lumen for at least a sufficient time to cause the obstructed material to remain compressed against the lumen wall. The catheter may be left in place with the wire mesh tip in an expanded position for a period of up to about 48 hours, although that length of time is generally not required to cause a lasting compression of the obstructive material.

In those embodiments of the catheter which include means for delivery of radio frequency energy to the obstruction in order to cut or ablate the mass of obstructive material, radio frequency energy is applied only for a sufficiently long period of time to cut or ablate the material, which is generally not longer than several minutes, although the catheter may be left in position with the wire mesh tip in its expanded position for a longer period of time of up to about 48 hours, in order to continue to compress any remaining obstructive material against the wall of the lumen to increase the flow path through the lumen.

All embodiments of the catheter according to the present invention can also be utilized with and include as an element thereof, a guidewire to facilitate placement of the catheter into the lumen of the vessel and advancement of the catheter to the situs of the obstruction. A guidewire lumen must be provided through the catheter from its proximal to its distal end to accommodate the guidewire. In those embodiments which utilize a control wire-plate mechanism to manipulate the wire mesh tip, the control wire can be a hollow tube and the plate has a hole through it to accommodate the guidewire.

When a guidewire is utilized, the above-described method of use of each embodiment of catheter equipped with a guidewire is preceded by an initial step, performed before insertion of the catheter into the lumen of the vessel, of inserting the guidewire into the lumen and advancing it through the lumen to the situs of the obstruction with at least a portion of the guidewire remaining external to the lumen at the point of insertion. The catheter is then placed on the guidewire and advancement of the catheter in the lumen to the situs of the obstruction according to the above-described methods of use proceeds along the guidewire.

All embodiments of the catheter according to the present invention can also include means for suctioning debris and fluids from the situs of removal of the obstructive mass through the catheter.

All embodiments of the catheter according to the present invention which utilize wire mesh tip control means, such as a control element-plate, and wherein the wire mesh tip extends beyond the distal end of the tubular catheter body when the tip is in a contracted position, with the wire mesh tip being unsheathed, can also be fitted with a slidable sheath to cover the wire mesh tip during insertion of the catheter to prevent the wire mesh tip from damaging the lumen of the vessel. Such a sheath is then retracted when the catheter is in place with the wire mesh tip at the situs at the obstruction before the wire mesh tip is expanded, and replaced when the catheter is to be withdrawn.

When the catheter is to be primed with one or more of a radiopaque contrasting solution to facilitate tracing its location; a saline solution to make it pH compatible with body fluids or blood in the vessel into which the catheter is to be inserted; or is to be created with a non-thrombogenic material to prevent blood clotting, such priming and/or coating steps are performed first, prior to insertion of the catheter into the vessel.

The foregoing embodiments of the wire mesh tipped catheter, its constituent elements and its method areas of use, according to the present invention, are not intended to be limiting. Further examples within the scope of the claims will be apparent to those skilled in the art.

We claim:

1. An apparatus for insertion into a tubular walled vessel of a living being, said tubular walled vessel having a lumen extending therethrough said tubular walled vessel further having a length, and an inner wall, and said lumen of said tubular walled vessel having a first, unobstructed inner diameter at which a maximum flowrate through said tubular walled vessel and said lumen occurs, and a second, obstructed inner diameter, less than said first inner diameter, at which a flowrate through said tubular walled vessel and said lumen less than said maximum flowrate occurs, said second inner diameter resulting from the presence of flow-obstructing material in said lumen on said inner wall of said tubular walled vessel over a portion of its said length, said apparatus being for enlarging an effective inner diameter of said lumen of said tubular walled vessel available for flow therein from said second inner diameter up to said first inner diameter by the compression and attenuation of said flow-obstructing material in said lumen, with said apparatus comprising, in combination:

(a). a tubular catheter body, open at both ends, with an inner diameter and an outer diameter, a fixed length, a proximal end, and a distal end, and an outer surface area;

(b). a flexible wire mesh tip for enlarging said effective inner diameter of said tubular walled vessel available for flow therein, by compressing said flow-obstructing material in said lumen against said inner wall of said tubular walled vessel, said wire mesh tip having a substantially cylindrical shape, with an inner surface area and an outer surface area, and with variable dimensions of diameter and length, both of which are determined by the configuration of said wire mesh tip in a position selected from the group (i–iii) consisting of: (i) a fully contracted position, (ii) a fully expanded position, and (iii) any one of a plurality of intermediate, partially expanded positions thereinbetween, with said wire mesh tip further having a proximal end and a distal end, said wire mesh tip being open at both ends, said wire mesh tip being fabricated from a wire mesh material having intrinsic shape-restoring properties caused by internal forces of said material which urge said wire mesh tip to assume a default position configuration in its said fully expanded position (ii), wherein said wire mesh tip has dimensions of a maximum, fully expanded diameter, such that said maximum, fully expanded diameter is greater than the diameter of said wire mesh tip in its said fully contracted position and not greater than thirty times said inner diameter of said tubular catheter body, and a fully expanded position length which is a minimum possible length of said wire mesh tip; with said wire mesh tip further being fabricated such that it assumes its said fully contracted position (i) when it is acted upon by external restraining forces sufficient to prevent said internal forces of said shape-restoring material of said wire mesh tip from causing said wire mesh tip to expand transversely in the direction of its said diameter, and such that said external restraining forces are sufficient to cause said wire mesh tip to be configured to have dimensions of a diameter not greater than said inner diameter of said tubular catheter body, and a fully contracted position length which is greater than said length of said wire mesh tip in its said fully expanded position, and is a maximum length of said wire mesh tip; and with said wire mesh tip still further being fabricated such that it assumes any one of a plurality of intermediate, partially expanded positions (iii), between said fully contracted position and said fully expanded position, wherein said wire mesh tip is acted upon by external restraining forces which are sufficient to prevent it from expanding to its said fully expanded position, but insufficient to hold it in its said fully contracted position, such that in any of said intermediate, partially expanded positions, said wire mesh tip is configured to have dimensions of a variable diameter that is between its said fully contracted diameter and its said fully expanded diameter, said intermediate, partially expanded diameter being determined by and being inversely proportional to said external restraining forces acting upon said wire mesh tip in its particular said intermediate, partially expanded position, and a variable partially expanded length that is between said length of said wire mesh tip in its said fully contracted position and said length of said wire mesh tip in its said fully expanded position;

(c). a wire mesh tip guide element, cooperating with said wire mesh tip, said wire mesh tip guide element being selected from the group (i–iii) consisting of (i) a rod, (ii) a tube, and (iii) an open coil, said wire mesh tip guide element having a proximal end and a distal end, said wire mesh tip guide element being positioned inside said tubular catheter body, and being slidable with respect thereto, with said distal end of said wire mesh tip guide element being attached to said proximal end of said wire mesh tip, said wire mesh tip guide element being longitudinally moveable within said tubular catheter body so as to cause corresponding movement of said wire mesh tip, such that said wire mesh tip is deployed out of said tubular catheter body when said wire mesh tip guide element is advanced in the direction of the distal end of said tubular catheter body, and further such that said wire mesh tip is retracted within said tubular catheter body when said wire mesh tip guide element is retracted in the direction of said proximal end of said tubular catheter body;

(d). a drawstring, having a proximal end, a distal end, and a length, such that said drawstring is positioned in a way selected from the group (i–iii) consisting of: (i) through said tube or said open coil and (ii) adjacent to said tube or said open coil, when said tube or said open coil is selected as said wire mesh tip guide element, and (iii) adjacent to said rod, when said rod is selected as said wire mesh tip guide element; such that a portion of said length of said drawstring, at said distal end thereof, is attached to said wire mesh material of said wire mesh tip, said drawstring being for manipulating the configuration of said wire mesh tip, when said wire mesh tip is deployed outside said tubular catheter body, by providing external restraining forces on said wire mesh tip, to enable said wire mesh tip to be reconfigured between different first and second configurations of said wire mesh tip selected from the group (i–iii) consisting of: (i) its said fully contracted position, (ii) its said fully expanded position, and (iii) any of its said intermediate, partially expanded positions thereinbetween, by the exertion of a variable pulling force on said drawstring, such that the degree of expansion of said wire mesh tip is inversely proportional to said variable pulling force exerted on said drawstring;

said apparatus being still further comprised such that said tubular catheter body is slidable relative to said wire mesh tip guide element and said wire mesh tip, with said tubular catheter body functioning as an outer sheath capable of surrounding said wire mesh tip and exerting an external restraining force on said wire mesh tip, to hold it in its said fully contracted position when said wire mesh tip is retracted within said tubular catheter body, said external restraining force of said tubular catheter body on said wire mesh tip thereby maintaining said wire mesh tip in its said fully contracted position without the need for a further external restraining force from said drawstring acting on said wire mesh tip, such that said tubular catheter body has a first position relative to said wire mesh tip guide element and said wire mesh tip, in which said tubular catheter body sheathes said wire mesh tip guide element and said wire mesh tip in its said fully contracted position, and said tubular catheter body has a second position in which said tubular catheter body does not sheath said wire mesh tip guide element and said wire mesh tip, when said wire mesh tip is deployed outside of said tubular catheter body with said wire mesh tip guide element;

(e). a wire for transmitting electromagnetic energy in the radio frequency range into said flow-obstructing material in said lumen of said vessel, to cause an attenuation of said flow-obstructing material, said wire extending the length of said tubular catheter body from the proximal end thereof to the distal end thereof, said wire being positioned in an annulus formed between said inner diameter of said tubular catheter body and said wire mesh tip guide element, said wire being connected at a distal end thereof to said wire mesh tip; and (f). a source for generating electromagnetic energy in the radio frequency range, said source being connected to said wire for transmitting electromagnetic energy at a proximal end thereof, external to said proximal end of said tubular catheter body.

2. The apparatus according to claim 1 wherein the wire mesh material of said wire mesh tip is fabricated in a braided, woven or knot pattern.

3. The apparatus according to claim 1 wherein the wire mesh material of said wire mesh tip has a mesh size that is permeable to the flow of fluid present in the lumen of the vessel in which said apparatus is deployed.

4. The apparatus according to claim 1 wherein the wire mesh of said wire mesh tip is fabricated from a metal or plastic that is inert to fluid present in the lumen of the vessel in which said apparatus is deployed.

5. The apparatus according to claim 4 wherein the wire mesh of said wire mesh tip is fabricated from a material selected from the group consisting of stainless steel, nitinol, (nickel-titanium alloy), titanium, vitallium and polyethylene.

6. The apparatus according to claim 1 wherein said wire for transmitting electromagnetic energy in the radio frequency range is a main transmitting wire which is connected to said wire mesh tip at a plurality of points of attachment on the outer surface of said wire mesh, through a corresponding number of branch transmitting wires extending from said main transmitting wire to said points of attachment.

7. The apparatus according to claim 1 further comprising a guidewire running through said apparatus, over which said apparatus is advanced, for facilitating placement of said apparatus in said lumen of said vessel.

8. The apparatus according to claim 1 in which at least a part of said outer surface area of said tubular catheter body and said outer surface area and said inner surface area of said wire mesh tip, all of which come into contact with blood in said lumen of said vessel, are coated with at least one of a non-thrombogenic material and an elastomeric material.

9. The apparatus according to claim 1 wherein said wire mesh tip is at least partially covered with an elastomeric material.

10. The apparatus according to claim 9 wherein said elastomeric material is selected from the group consisting of thermoplastic elastomers and silicone.

11. The apparatus according to claim 10 wherein said thermoplastic elastomers include polyurethane and polyethylene.

12. The apparatus according to claim 1 wherein said wire mesh tip is reconfigurable according to one of the configuration transitions selected from the group (i–vi) consisting of: (i) from its said fully contracted position through a plurality of intermediate positions to its said fully expanded position; (ii) from its said fully expanded position through a plurality of intermediate positions to its said fully contracted position; (iii) from a first one of said plurality of intermediate positions to a second one of said plurality of intermediate positions which is more expanded than said first intermediate position when said restraining forces exerted upon said wire mesh tip are reduced in reconfiguring said wire mesh tip from its first said intermediate position to its said second intermediate position; (iv) from a first one of said plurality of intermediate positions to a second one of said plurality of intermediate positions which is more contracted than said first intermediate position when said restraining forces exerted upon said wire mesh tip are increased in reconfiguring said wire mesh tip from its first said intermediate position to its said second intermediate position; (v) from an intermediate position to said fully contracted position; and (vi) from an intermediate position to said fully expanded position;

the position and state of configuration of said wire mesh tip with respect to its expansion or contraction being proportional to said pulling force being exerted on said main control element through said remote control means.

13. The apparatus according to claim 1 further comprised by:

an ablation electrode for attenuating said flow-obstructing material in said lumen of said vessel by at least one means selected from the group (i–ii) consisting of (i) cutting said flow-obstructing material and (ii) ablating said flow-obstructing material, said ablation electrode being attached to said distal end of said wire mesh tip, with said ablation electrode being electrically insulated from said wire mesh tip;

a wire for transmitting electrical energy to said ablation electrode, said wire extending through said length of said tubular catheter body from said proximal end thereof, in an annular space formed between an inner wall of said tubular catheter body and said wire mesh tip guide element, which is positioned inside said tubular catheter body and which cooperates with said wire mesh tip, to said distal end of said wire mesh tip guide element, and then to said ablation electrode at said distal end of said wire mesh tip, said wire for transmitting electrical energy to said ablation electrode being electrically insulated from each of said tubular catheter body, said wire mesh tip guide element, said wire mesh tip, and said wire for transmitting radio frequency energy; and a source for generating electrical energy for said ablation electrode, connected to said wire for transmitting electrical energy to said ablation electrode, at said proximal end of said wire, external to said proximal end of said wire, and external to said proximal end of said tubular catheter body.

14. A method for enlarging an effective inner diameter of a lumen of a tubular walled vessel in a living being, said effective inner diameter of said lumen of said tubular walled vessel being available for flow therein, said tubular walled vessel having a length, and an inner wall, with said lumen of said tubular walled vessel extending said length thereof, and with said lumen of said tubular walled vessel having a first, unobstructed inner diameter at which a maximum flowrate through said tubular walled vessel and said lumen occurs, and a second, obstructed inner diameter, less than said first inner diameter, at which a flowrate through said tubular walled vessel and said lumen less than said maximum flowrate occurs, said second inner diameter resulting from the presence of flow-obstructing material in said lumen on said inner wall of said tubular walled vessel over a portion of its said length, said method comprising:

(a) inserting into said lumen of said tubular walled vessel an apparatus comprising, in combination:

(i) a tubular catheter body, open at both ends, with an inner diameter and an outer diameter, a fixed length, a proximal end and a distal end, and an outer surface area;

(ii) a flexible wire mesh tip for enlarging said effective inner diameter of said lumen of said tubular walled vessel available for flow therein, by compressing said flow-obstructing material in said lumen, said wire mesh tip having a substantially cylindrical shape, with an inner surface area and an outer surface area, and with variable dimensions of diameter and length, both of which are determined by the configuration of said wire mesh tip in a position selected from the group (i–iii) consisting of: (i) a fully contracted position, (ii) a fully expanded position, and (iii) any one of a plurality of intermediate, partially expanded positions thereinbetween, with said wire mesh tip further having a proximal end and a distal end, said wire mesh tip being open at both ends, said wire mesh tip being fabricated from a wire mesh material having intrinsic shape-restoring properties caused by internal forces of said material which urge said wire mesh tip to assume a default position configuration in its said fully expanded position (ii), wherein said wire mesh tip has dimensions of a maximum, fully expanded diameter, such that said maximum, fully expanded diameter is greater than the diameter of said wire mesh tip in its said fully contracted position and not greater than thirty times said inner diameter of said tubular catheter body, and a fully expanded position length which is a minimum possible length of said wire mesh tip; with said wire mesh tip being further fabricated so that it assumes its said fully contracted position (i) when it is acted upon by external restraining forces sufficient to prevent said internal forces of said shape-restoring material of said wire mesh tip from causing said wire mesh tip to expand transversely in the direction of its said diameter, and such that said external restraining forces are sufficient to cause said wire mesh tip to be configured to have dimensions of a diameter not greater than said inner diameter of said tubular catheter body, such that said wire mesh tip, when in its said fully contracted position, is longitudinally moveable inside said tubular catheter body, and a fully contracted position length which is greater than said length of said wire mesh tip in its said fully expanded position, and is a maximum effective length of said wire mesh tip; and with said wire mesh tip still further being fabricated such that it assumes any one of a plurality of intermediate, partially expanded positions (iii), between said fully contracted position and said fully expanded position, wherein said wire mesh tip is acted upon by external restraining forces which are sufficient to prevent it from expanding to its said fully expanded position, but insufficient to hold it in its said fully contracted position, such that in any of said intermediate, partially expanded positions, said wire mesh tip is configured to have dimensions of a variable diameter that is between its said fully contracted diameter and its said fully expanded diameter, said intermediate, partially expanded diameter being determined by and being inveresly proportional to said external restraining forces acting upon said wire mesh tip in its particular said intermediate, partially expanded position, and a variable partially expanded length that is between said length of said wire mesh tip in its said fully contracted position and said length of said wire mesh tip in its said fully expanded position;

(iii) a wire mesh tip guide element, cooperating with said wire mesh tip, said wire mesh tip guide element being selected from the group (i–iii) consisting of (i) a rod, (ii) a tube, and (iii) an open coil, said wire mesh tip guide element having a proximal end and a distal end, said wire mesh tip guide element being positioned inside said tubular catheter body, and being slidable with respect thereto, with said distal end of said wire mesh tip guide element being attached to said proximal end of said wire mesh tip, said wire mesh tip guide element being longitudinally moveable within said tubular catheter body so as to cause corresponding movement of said wire mesh tip, such that said wire mesh tip is deployed out of said tubular catheter body when said wire mesh tip guide element is advanced in the direction of the distal end of said tubular catheter body, and further such that said wire mesh tip is retracted within said tubular catheter body when said wire mesh tip guide element is retracted in the direction of said proximal end of said tubular catheter body;

(iv) a drawstring, having a proximal end, a distal end, and a length, such that said drawstring is positioned in a way selected from the group (i–iii) consisting of: (i) through said tube or said open coil and (ii) adjacent to said tube or said open coil, when said tube or said open coil is selected as said wire mesh tip guide element, and (iii) adjacent to said rod, when said rod is selected as said wire mesh tip guide element; such that a portion of said length of said drawstring, at said distal end thereof, is woven into said wire mesh material of said wire mesh tip, said drawstring being for manipulating the configuration of said wire mesh tip, when said wire mesh tip is deployed outside said tubular catheter body, back and forth between its said fully contracted position and its said fully expanded position or any one of its said intermediate, partially expanded positions thereinbetween, by exerting an external restraining force on said wire mesh tip, such that in order to cause said wire mesh tip to assume another position selected from its said fully contracted position and one of its said intermediate, partially expanded positions, a pulling force is exerted on said drawstring, said pulling force being translated into an external restraining force on said wire mesh tip to pull said wire mesh tip in a direction toward said proximal end of said tubular catheter body, thereby causing said variable diameter of said wire mesh tip to decrease, and, in turn, causing said variable length of said wire mesh tip to increase, the change in each said dimension being in proportion to the magnitude of the pulling force exerted on said drawstring;

said apparatus being still further comprised such that said tubular catheter body is slidable relative to said wire mesh tip guide element and said wire mesh tip, with said tubular catheter body functioning as an outer sheath for surrounding said wire mesh tip and exerting an external restraining force on said wire mesh tip, to hold it in its said fully contracted position when said wire mesh tip is retracted within said tubular catheter body, said external restraining force of said tubular catheter body on said wire mesh tip thereby maintaining said wire mesh tip in its said fully contracted position without the need for a further external restraining force from said drawstring acting on said wire mesh tip, such that said tubular catheter body has a first position relative to said wire mesh tip guide element and said wire mesh tip, in which said tubular catheter body sheathes said wire mesh tip guide element and said wire mesh tip in its said fully contracted position, and said tubular catheter body has a second position in which said tubular catheter body does not sheath said wire mesh tip guide element and said wire mesh tip, when said wire mesh tip is deployed outside of said tubular catheter body with said wire mesh tip guide element;

(v) a wire for transmitting electromagnetic energy in the radio frequency range into said flow-obstructing material in said lumen of said tubular walled vessel, to cause an attenuation of said flow-obstructing material by fracturing a portion of said flow-obstructing material, said wire extending the length of said tubular catheter body from the proximal end thereof to the distal end thereof, said wire being positioned in an annulus formed between said inner diameter of said tubular catheter body and said wire mesh tip guide element, said wire being connected at a distal end thereof to said wire mesh tip, and said wire being electrically insulated from said tubular catheter body, said wire mesh tip guide element, and said wire mesh tip; and (vi) a source for generating electromagnetic energy in the radio frequency range, said source being connected to said wire for transmitting electromagnetic energy at a proximal end thereof, external to said proximal end of said tubular catheter body;

(b) advancing said apparatus through said lumen of said tubular walled vessel so that said distal end of said tubular catheter body of said apparatus is positioned at or proximal to said flow-obstructing material, such that where said flow-obstructing material occludes said lumen of said vessel to an extent that the effective diameter of said lumen available for flow therethrough is smaller than said outer diameter of said tubular catheter body of said apparatus, said apparatus is positioned in said lumen of said vessel such that said distal end of said tubular catheter body of said apparatus is proximal to said flow-obstructing material; and where said flow-obstructing material occludes said lumen of said vessel to an extent that the effective diameter of said lumen available for flow therethrough is larger than said outer diameter of said tubular catheter body of said apparatus, said apparatus is positioned in said lumen of said vessel such that said distal end of said tubular catheter body of said apparatus is within said flow-obstructing material;

(c) sliding said wire mesh tip guide element relative to said tubular catheter body in a direction toward said distal end of said tubular catheter body to cause said wire mesh tip to be deployed outside of said tubular catheter body, while maintaining a pulling force on said drawstring to prevent said wire mesh tip from suddenly expanding to one of its said partially-expanded positions or to its said fully expanded position, (d) actuating said source for generating electromagnetic energy in the radio frequency range to cause electromagnetic energy to flow into said wire for transmitting electromagnetic energy;

(e) transmitting said electromagnetic energy in the radio frequency range from said distal end of said wire for transmitting electromagnetic energy into said flow-obstructing material in said lumen of said vessel for a sufficiently long period of time to cause attenuation of said flow-obstructing material by fracturing a portion thereof, and to cause an increase in the effective inner diameter of said lumen for flow therethrough, such that said flow-obstructing material is attenuated to an extent that said effective inner diameter of said lumen for flow therethrough is at least as large as said outer diameter of said tubular catheter body of said apparatus;

(f) halting the transmission of said electromagnetic energy in the radio frequency range into a remaining portion of said flow-obstructing material in said lumen of said vessel from said wire for transmitting electromagnetic energy;

(g) deactuating said source for generating electromagnetic energy in the radio frequency range;

(h) where said flow-obstructing material occluded said lumen of said vessel to an extent that the effective diameter of said lumen available for flow therethrough was smaller than said outer diameter of said tubular catheter body of said apparatus, and said apparatus was positioned in said lumen of said vessel such that said distal end of said tubular catheter body of said apparatus was proximal to said flow-obstructing material, advancing said apparatus in said lumen of said vessel such that said wire mesh tip is positioned within said remaining portion of said flow-obstructing material after attenuation thereof by said electromagnetic energy in the radio frequency range; and where said flow-obstructing material occluded said lumen of said vessel to an extent that the effective inner diameter of said lumen available for flow therethrough was larger than said outer diameter of said tubular catheter body of said apparatus, and said apparatus is positioned in said lumen of said vessel such that said distal end of said tubular catheter body of said apparatus is within said remaining portion of said flow-obstructing material after attenuation thereof by said electromagnetic energy in the radio frequency range, said apparatus is retained in said position;

(i) gradually removing said pulling force on said drawstring, to cause said wire mesh tip to be reconfigured to an expanded position within said remaining portion of said flow-obstructing material, such that said wire mesh tip has an expanded diameter greater than its contracted diameter and not greater than thirty times said outer diameter of said tubular catheter body and a length equal to an expanded length in the axial direction of said tubular catheter body that is shorter than said contracted length, the expansion of said diameter of said wire mesh tip at said flow-obstructing material being sufficient to produce a compression of said remaining portion of said flow-obstructing material against said tubular wall of said lumen to further increase said effective inner diameter of said lumen available for flow therethrough;

(j) allowing said expanded wire mesh tip to remain in an expanded position in said lumen of said vessel, wherein said remaining portion of said flow-obstructing material is compressed against said tubular wall of said lumen, for a sufficient period of time to prevent said remaining portion of said flow-obstructing material from re-expanding to again reduce said effective inner diameter of said lumen of said vessel;

(k) increasing said pulling force on said drawstring to cause said wire mesh tip to be returned to its said fully contracted position;

(l) sliding said wire mesh tip guide element relative to said tubular catheter body in a direction toward said proximal end of said tubular catheter body to cause said fully contracted wire mesh tip to be retracted into said distal end of said tubular catheter body and to be sheathed therewithin; and (m) withdrawing said apparatus from said lumen of said vessel.

15. The method according to claim 14 wherein said apparatus remains in place in said lumen of said vessel, with said wire mesh tip in an expanded position, for a period of time of up to about 48 hours, during which time said flow-obstructing material is compressed against said inner wall of said tubular walled vessel by said wire mesh tip, in order to increase said effective inner diameter of said lumen of said vessel available for flow therein.

16. The method according to claim 14 wherein said apparatus remains in place in said lumen of said vessel, with said wire mesh tip in an expanded position, for a period of time of up to about 48 hours, in order to compress said flow-obstructing material against said inner wall of said tubular walled vessel, thereby increasing said effective inner diameter of said lumen of said vessel available for flow therein, with radio frequency energy being supplied to said wire mesh tip of said apparatus only for a shorter duration during said period of time as is required to attenuate at least a portion of said flow obstructing material.

17. The method according to claim 14 further comprising steps, performed before step (a), of:

(a') inserting a guidewire into said lumen of said vessel and advancing said guidewire through said lumen to said flow-obstructing material, such that at least a portion of said guidewire remains external to said lumen at the point of insertion; and (a") placing said apparatus of step (a) onto said guidewire; and further that said method is such that the insertion in step (a) and the advancement in step (b) of said apparatus is done along said guidewire.

18. The method according to claim 14, further comprising a step, performed before step (a), of coating at least one outer surface area of said apparatus selected from said outer surface area of said tubular catheter body and said external surface area of said wire mesh tip with at least one of a radiopaque contrasting solution, a saline solution, and a non-thrombogenic material before insertion of aid apparatus into said lumen of said vessel.

19. The method according to claim 17, further comprising a step, performed before step (a'), of coating at least one outer surface area said apparatus of step (a), selected from said outer surface area of said tubular catheter body and said external surface area of said wire mesh tip, with at least one of a radiopaque contrasting solution, a saline solution, and a non-thrombogenic material.

20. A method for removing a flow obstruction from the lumen of a tubular walled vessel in a living being, said tubular walled vessel having a lumen extending therethrough, said method comprising:

(a) inserting into said lumen of said tubular walled vessel an apparatus comprising, in combination, the elements (i–ix):

(i) a tubular catheter body, open at both ends, with an inner diameter and an outer diameter, a fixed length, and a proximal end and a distal end;

(ii) a flexible wire mesh tip for enlarging said effective inner diameter of said lumen of said tubular walled vessel available for flow therein, by compressing said flow-obstructing material in said lumen, said wire mesh tip having a substantially cylindrical shape, with an inner surface area and an outer surface area, and with variable dimensions of diameter and length, both of which are determined by the configuration of said wire mesh tip in a position selected from the group (A–C) consisting of: (A) a fully contracted position, (B) a fully expanded position, and (C) any one of a plurality of intermediate, partially expanded positions thereinbetween, said wire mesh tip further having a proximal end and a distal end, said wire mesh tip being open at both ends, said wire mesh tip being fabricated from a wire mesh material having intrinsic shape-restoring properties caused by internal forces of said material which urge said wire mesh tip to assume a default position configuration in its said fully expanded position (B), wherein said wire mesh tip has dimensions of a maximum, fully expanded diameter, such that said maximum, fully expanded diameter is greater than the diameter of said wire mesh tip in its said fully contracted position and not greater than thirty times said inner diameter of said tubular catheter body, and a fully expanded position length which is a minimum possible length of said wire mesh tip; with said wire mesh tip being further fabricated so that it assumes its said fully contracted position (A) when it is acted upon by external restraining forces sufficient to prevent said internal forces of said shape-restoring material of said wire mesh tip from causing said wire mesh tip to expand transversely in the direction of its said diameter, and such that said external restraining forces are sufficient to cause said wire mesh tip to be configured to have dimensions of a diameter not greater than said inner diameter of said tubular catheter body, such that said wire mesh tip, when in its said fully contracted position, is longitudinally moveable inside said tubular catheter body, and a fully contracted position length which is greater than said length of said wire mesh tip in its said fully expanded position, and is a maximum effective length of said wire mesh tip; and with said wire mesh tip still further being fabricated such that it assumes any one of a plurality of intermediate, partially expanded positions (C), between said fully contracted position and said fully expanded position, wherein said wire mesh tip is acted upon by external restraining forces which are sufficient to prevent it from expanding to its said fully expanded position, but insufficient to hold it in its said fully contracted position, such that in any of said intermediate, partially expanded positions, said wire mesh tip is configured to have dimensions of a variable diameter that is between its said fully contracted diameter and its said fully expanded diameter, said intermediate, partially expanded diameter being determined by and being inveresly proportional to said external restraining forces acting upon said wire mesh tip in its particular said intermediate, partially expanded position, and a variable partially expanded length that is between said length of said wire mesh tip in its said fully contracted position and said length of said wire mesh tip in its said fully expanded position;

(iii) a wire mesh tip guide element, cooperating with said wire mesh tip, said wire mesh tip guide element being selected from the group consisting of a rod, a tube and an open coil, said wire mesh tip guide element having a proximal end and a distal end, said wire mesh tip guide element being positioned inside said tubular catheter body, and being slidable with respect thereto, with said distal end of said wire mesh tip guide element being attached to said proximal end of said wire mesh tip, said wire mesh tip guide element being capable of longitudinal movement within said tubular catheter body so as to cause corresponding movement of said wire mesh tip, alternatively deploying said wire mesh tip out of said tubular catheter body when said wire mesh tip guide element is advanced in the direction of the distal end of said tubular catheter body, and retracting said wire mesh tip within said tubular catheter body when said wire mesh tip guide element is retracted in the direction of said proximal end of said tubular catheter body;

(iv) a drawstring, having a proximal end, a distal end, and a length, such that said drawstring alternatively passes through or adjacent to said tube or open coil, when said tube or open coil is selected as said wire mesh tip guide element, and adjacent to said rod, when said rod is selected as said wire mesh tip guide element; such that a portion of said length of said drawstring, at said distal end thereof, is woven into said wire mesh material of said wire mesh tip, said drawstring being for manipulating the configuration of said wire mesh tip, when said wire mesh tip is deployed outside said tubular catheter body, back and forth between its said fully contracted position and its said fully expanded position or any one of its said intermediate, partially expanded positions thereinbetween, by exerting an external restraining force on said wire mesh tip, such that in order to cause said wire mesh tip to assume its said fully contracted position or one of its said intermediate, partially expanded positions, a pulling force is exerted on said drawstring, said pulling force being translated into an external restraining force on said wire mesh tip to pull said wire mesh tip in a direction toward said proximal end of said tubular catheter body, thereby causing said variable diameter of said wire mesh tip to decrease, and, in turn, causing said variable length of said wire mesh tip to increase, the change in each said dimension being in proportion to the magnitude of the pulling force exerted on said drawstring;

said apparatus being still further comprised such that said tubular catheter body is slidable relative to said wire mesh tip guide element and said wire mesh tip, with said tubular catheter body functioning as an outer sheath which surrounds said wire mesh tip and exerts an external restraining force on said wire mesh tip, to hold it in its said fully contracted position when said wire mesh tip is retracted within said tubular catheter body, said external restraining force of said tubular catheter body on said wire mesh tip thereby maintaining said wire mesh tip in its said fully contracted position without the need for a further external restraining force from said drawstring acting on said wire mesh tip, such that said tubular catheter body has a first position relative to said wire mesh tip guide element and said wire mesh tip, in which said tubular catheter body sheathes said wire mesh tip guide element and said wire mesh tip in its said fully contracted position, and said tubular catheter body has a second position in which said tubular catheter body does not sheath said wire mesh tip guide element and said wire mesh tip, when said wire mesh tip is deployed outside of said tubular catheter body with said wire mesh tip guide element;

(v) an ablation electrode for attenuating said flow obstruction in said lumen of said vessel by at least one of the means of cutting and ablating a portion of said flow obstruction, said ablation electrode being attached to said distal end of said wire mesh tip, with said ablation electrode being electrically insulated from said wire mesh tip;

(vi) a wire for transmitting electrical energy to said ablation electrode, said wire extending through said length of said tubular catheter body from said proximal end thereof, in an annular space formed between an inner wall of said tubular catheter body and said wire mesh tip guide element, which is positioned inside said tubular catheter body, and cooperates with said wire mesh tip, to said distal end to said wire mesh tip guide element, and then to said ablation electrode at said distal end of said wire mesh tip, said wire for transmitting electrical energy to said ablation electrode being electrically insulated from each of said tubular catheter body, said wire mesh tip guide element, said wire mesh tip, and said wire for transmitting radio frequency energy;

(vii) a source for generating electrical energy for said ablation electrode, connected to said wire for transmitting electrical energy to said ablation electrode, at said proximal end of said wire, external to said proximal end of said wire, and external to said proximal end of said tubular catheter body;

(viii) a wire for transmitting electromagnetic energy in the radio frequency range into said flow obstruction in said lumen of said tubular walled vessel, to cause an attenuation of said obstruction by fracturing a portion thereof, said wire extending the length of said tubular catheter body from the proximal end thereof to the distal end thereof, said wire being positioned in an annulus formed between said inner diameter of said tubular catheter body and said wire mesh tip guide element, said wire being connected at a distal end thereof to said wire mesh tip, and said wire being electrically insulated from said tubular catheter body, said wire mesh tip guide element, and said wire mesh tip; and (ix) a source for generating electromagnetic energy in the radio frequency range, said source being connected to said wire for transmitting electromagnetic energy at a proximal end thereof, external to said proximal end of said tubular catheter body;

(b) advancing said apparatus through said lumen of said tubular walled vessel so that said distal end of said tubular catheter body of said apparatus is positioned at or proximal to said flow obstruction, in a manner selected from the group (i–ii) consisting of (i) positioning said apparatus in said lumen of said vessel such that said distal end of said tubular catheter body of said apparatus with said ablation electrode is proximal to said flow obstruction when said flow obstruction occludes said lumen of said vessel to an extent that the effective diameter of said lumen available for flow therein is smaller than said outer diameter of said tubular catheter body of said apparatus; and (ii) positioning said apparatus in said lumen of said vessel such that said distal end of said tubular catheter body of said apparatus is within said flow obstruction when said flow obstruction occludes said lumen of said vessel to an extent that the effective diameter of said lumen available for flow therein is larger than said outer diameter of said tubular catheter body of said apparatus;

(c) sliding said wire mesh tip guide element relative to said tubular catheter body in a direction toward said distal end of said tubular catheter body to cause said wire mesh tip to be deployed outside of said tubular catheter body, while maintaining a pulling force on said drawstring to prevent said wire mesh tip from suddenly expanding to one of its said partially-expanded positions or to its said fully expanded position;

where said apparatus is positioned according to (b) (i), performing (d)–(g);

(d) actuating said source for generating electrical energy for said ablation electrode to cause a flow of electrical energy into said ablation electrode;

(e) transmitting said electrical energy from said ablation electrode into said flow obstruction in said lumen of said vessel for a sufficiently long period of time to cause attenuation of said flow obstruction by the cutting or ablation of at least a portion of said obstruction, and an increase in the effective diameter of said lumen for flow therethrough, such that said flow obstruction is attenuated to an extent that the effective diameter of said lumen for flow therethrough is at least as large as said outer diameter of said tubular catheter body of said apparatus;

(f) halting the transmission of said electrical energy into said flow obstruction in said lumen of said vessel from said ablation electrode;

(g) deactuating said source for generating electrical energy for said ablation electrode;

(h) advancing said apparatus in said lumen of said vessel such that said wire mesh tip is positioned within a remaining portion of said flow obstruction after attenuation thereof by said ablation electrode; and where said apparatus is positioned according to (b) (ii), performing (i)–(l);

(i) actuating said source for generating electromagnetic energy in the radio frequency range to cause electromagnetic energy to flow into said wire for transmitting electromagnetic energy;

(j) transmitting said electromagnetic energy in the radio frequency range from said distal end of said wire for transmitting electromagnetic energy into said obstruction in said lumen of said vessel for a sufficiently long period of time to cause attenuation of said obstruction and an increase in the effective diameter of said lumen for flow therethrough, such that said obstruction is attenuated to an extent that the effective diameter of said lumen for flow therethrough is at least as large as said outer diameter of said tubular catheter body of said apparatus;

(k) halting the transmission of said electromagnetic energy in the radio frequency range into said obstruction in said lumen of said vessel from said wire for transmitting electromagnetic energy;

(l) deactuating said source for generating electromagnetic energy in the radio frequency range;

(m) gradually removing said pulling force on said drawstring, to cause said wire mesh tip to be reconfigured to an expanded position within said remaining portion of said flow obstruction, such that said wire mesh tip has an expanded diameter greater than its contracted diameter and not greater than thirty times said outer diameter of said tubular catheter body and a length equal to an expanded length in the axial direction of said tubular catheter body that is shorter than said contracted length, the expansion of said diameter of said wire mesh tip at said flow obstruction being sufficient to produce a compression of said remaining portion of said flow obstruction against said tubular wall of said lumen to further increase the effective diameter of said lumen available for flow therethrough;

(n) allowing said expanded wire mesh tip to remain in an expanded position in said lumen of said vessel, wherein said remaining portion of said flow obstruction is compressed against said tubular wall of said lumen, for a sufficient period of time to prevent said remaining portion of said flow obstruction from re-expanding to again reduce said effective diameter of said lumen of said vessel;

(o) increasing said pulling force on said drawstring to cause said wire mesh tip to be returned to its said fully contracted position;

(p) sliding said wire mesh tip guide element relative to said tubular catheter body in a direction toward said proximal end of said tubular catheter body to cause said fully contracted wire mesh tip to be retracted into said distal end of said tubular catheter body and to be sheathed therewithin; and (q) withdrawing said apparatus from said lumen of said vessel.

21. The method according to claim 57, further comprising priming said tubular catheter body of said apparatus with at least one of a radiopaque contrasting solution, a saline solution, and a non-thrombogenic material before insertion of said apparatus into said lumen of said vessel.

\* \* \* \* \*